(12) United States Patent
Dean et al.

(10) Patent No.: US 6,509,001 B1
(45) Date of Patent: *Jan. 21, 2003

(54) CALCITONIN RECEPTOR BINDING REAGENTS

(75) Inventors: Richard T. Dean, Bedford, NH (US);
Larry R. Bush, Exeter, NH (US);
Daniel A. Pearson, Bedford, NH (US);
John Lister-James, Bedford, NH (US)

(73) Assignee: Diatide, Inc., Londonderry, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,494

(22) Filed: Apr. 20, 2000

Related U.S. Application Data

(60) Division of application No. 09/071,090, filed on May 1, 1998, now Pat. No. 6,086,850, which is a continuation-in-part of application No. 08/847,007, filed on May 1, 1997, now Pat. No. 6,083,480.

(51) Int. Cl.[7] .................. A61K 51/00; A61M 36/14
(52) U.S. Cl. ............... 424/1.69; 424/1.11; 424/1.65; 424/9.1; 534/14; 530/317; 530/300
(58) Field of Search ............... 424/1.11, 1.65, 424/1.69, 9.1, 9.3, 9.4, 9.5, 1.49, 1.53, 9.2; 534/7, 10–16; 530/300, 311, 317, 324–330, 333, 334, 338; 206/223, 569, 570; 514/13

(56) References Cited

U.S. PATENT DOCUMENTS

| 4,086,221 A | | 4/1978 | Sakakibara et al. | |
| 4,277,393 A | | 7/1981 | Sakakibara et al. | |
| 5,541,159 A | | 7/1996 | Albert et al. | |
| 6,083,480 A | * | 7/2000 | Dean et al. | 424/1.69 |
| 6,086,850 A | * | 7/2000 | Dean et al. | 424/1.69 |

FOREIGN PATENT DOCUMENTS

| EP | 0 181 121 A3 | 5/1986 |
| EP | 0 347 105 A2 | 12/1989 |
| EP | 0 315 687 B1 | 1/1994 |
| EP | 0 370 165 B1 | 1/1994 |
| WO | WO 94/18959 | 9/1994 |
| WO | WO 95/33497 | 12/1995 |
| WO | WO 96/04308 | 2/1996 |

OTHER PUBLICATIONS

Cohen, et al. (1996) "Iodocalcitonin Binds to Human Calcitonin Receptors with Higher Affinity than Calcitonin" Endocrinology, 137, 4507–4510.

Findlay, et al. (1981) "Calcitonin Binding and Degradation by Two Cultured Human Breast Cancer Cell Lines (MCF 7 and T 47D)" Biochem. Jnl., 196, 513–520.

Paulin, et al. , (1978) "Preliminary Study on Synthetic Calcitonin in the Rabbit and in Man" Bull. Soc. Med. Afr. Noire Lgue Frxe, 23, 246–251.

Potts, John T. Jr., (1992) "Chemistry of the Calcitonins" Bone and Mineral, 16 169–173.

Zaidi, et al., (1987) "Biology of Peptides from the Calcitonin Genes" Quarterly Jnl. of Experimental Physiology, 72, 371–408.

Yates, et al. (1990) A Noncyclical Analog of Salmon Calcitonin (N –Propionyl Di–Ala ,des–Leu sCT) Retains Full Potency without Inducing Anorexia in Rats.

* cited by examiner

*Primary Examiner*—Dameron L. Jones
(74) *Attorney, Agent, or Firm*—Millen, White, Zelano & Branigan, P.C.

(57) ABSTRACT

This invention relates to calcitonin receptor binding reagents Comprising Compounds which are Covalently linked to a radiometal chelator. The invention is embodied as calcitonin receptor binding peptide derivatives and analogues of calcitonin which may be radiolabeled with a suitable isotope and used as radiodiagnostic or radiotherapeutic agents. Methods and kits for making, radiolabeling and using such reagents diagnostically and therapeutically in a mammalian body are also provided.

20 Claims, No Drawings

CALCITONIN RECEPTOR BINDING REAGENTS

This application is a divisional of allowed U.S. application Ser. No. 09/071,090, filed May 1, 1998, now U.S. Pat. No. 6,086,850 which is a Continuation-in-part of U.S. application Ser. No. 08/847,007, filed May 1, 1997 now U.S. Pat. No. 6,083,480.

This invention relates to calcitonin receptor binding reagents which are capable of complexing with metal ions, including radioactive metal ions, and to labeled embodiments of such reagents for use in imaging sites in a mammalian body or for use in therapy, particularly for use in cancer therapy.

BACKGROUND OF THE INVENTION

Great strides have been made over the past 60 years in reducing long-term mortality trends for some types of cancer, such as stomach cancer. However, during the same period, mortality trends for other cancers have remained stable or increased. For example, lung cancer is the most frequent cancer worldwide, representing the leading cause of cancer mortality among men and women. Breast cancer is the commonest cancer among women and the second leading cause of cancer mortality in women, and ovarian cancer mortality rates are increasing in some countries. childhood and adult lymphatic cancers, such as leukemias and non-Hodgkin's lymphomas, also continue to represent significant causes of cancer mortality. Early diagnosis and effective treatment remains a goal for all of these cancers.

Several years ago, site directed diagnosis and therapy were proposed, to allow in vivo targeting of particular sites of disease within an animal's body. In general, site-directed diagnosis or therapy employs a targeting moiety, such as an antibody specific for the disease site or for the organism which caused the disease, coupled to a label in the case of a diagnostic agent or to a cytotoxic agent in the case of a therapeutic agent. A very large body of literature exists relating to radiolabeling antibodies or antibody fragments for diagnostic imaging purposes. Similarly, a number of site directed therapeutic agents employing monoclonal antibodies and a variety of radioisotopes have been proposed over the years, e.g., as set forth in U.S. Pat. Nos. 4,454,106; 4,472,509; 4,828,991; 5,246,691; 5,355,394; and 5,641,471; in EP 429624; EP 585986; WO 90/15625, and the like. Such antibody-based agents produce side effects related to the immune responses of the treated animal to the antibody, even if antibody fragments or humanized antibodies are employed as the targeting moiety.

The disadvantages of antibody-based site-directed diagnostic and therapeutic agents can be avoided when targeting moieties having lower molecular weights, such as receptor-specific peptides or small molecules are employed. However, coupling of a peptide or small molecule to a label or cytotoxic agent, while retaining the compound's receptor specificity, can be technically difficult. Methods for radiolabeling peptides and other small molecules which preserve the ability of the compound to bind specifically to a receptor are disclosed in commonly owned U.S. Pat. Nos. 5,225,180; 5,405,597; 5,443,815; 5,508,020; 5,552,525; 5,561,220; 5,620,675; 5,645,815; 5,654,272; 5,711,931; 5,716,596; 5,720,934; and 5,736,122; in abandoned U.S. patent application Ser. No. 07/955,466; and in WO92/13572, WO93/10747, WO93/17719, WO93/21962, WO93/23085, WO93/25244, WO94/00489, WO94/07918, and WO94/28942. The methods disclosed in these patents and publications are particularly suitable for manufacture of site-directed diagnostic imaging agents. Commonly assigned U.S. Pat. Nos. 5,620,675; 5,716,596; WO 94/00489; WO 95/03330; WO 95/00553; WO 95/31221; and WO 96/04308 disclose somatostatin peptide analogs which may be used for site-directed radiotherapy. Commonly assigned WO 95/33497 discloses somatostatin analogs, gpIIb/IIIa receptor-binding peptides, and leukocyte-binding peptides which may be used for site-directed radiodiagnosis or radiotherapy. Commonly assigned WO 96/30055 discloses vasoactive intestinal peptide (VIP) receptor-binding peptides which may be used for site-directed radiodiagnosis or radiotherapy.

Tumor cells often occasionally express or overexpress a particular receptor or receptor subtype, as indicated by receptor binding studies. In some types of cancer, tumor cell markers can change as the disease progresses, possibly reflecting the stage of the disease and thus the patient's prognosis. The kind of receptor that a tumor cell expresses can be characteristic of the tumor's etiology and can thus provide a relatively specific marker for the tumor. For example, radiolabeled somatostatin analogs have been shown to bind specifically to neuroendocrine tumors, melanomas, lung cancer, and certain breast cancers. One such analog, $^{111}$In-OCTREOSCAN, has received marketing approval for use in imaging neuroendocrine tumors. A second radiolabeled somatostatin analog, $^{99m}$Tc-Depreotide, has Completed Phase III clinical trials for use in imaging lung cancers. $^{123}$I-vasoactive intestinal peptide has been shown to target adenocarcinomas of the colon and stomach.

Calcitonin (CT) is a 32 amino acid peptide secreted from the thyroid in response to elevated serum calcium levels. Calcitonin has a number of biological effects, which are mediated by calcitonin receptors present on the surfaces of cells in the target organ. High affinity receptors for CT have been identified in bone, kidney, lung, and central nervous system. In bone, CT inhibits bone resorption by osteoclasts; in kidney, CT increases excretion of calcium ions; and in the central nervous system, the peptide induces analgesia, gastric acid secretion, and appetite inhibition. Small amounts of CT have been administered to animals and humans without toxic effects, and salmon CT is used clinically to treat such bone disorders as Paget's disease, hypercalcemia of malignancy, and osteoporosis. Intravenously-administered calcitonin clears the blood rapidly and is excreted primarily in urine. The major sites of localization for administered CT are kidney, liver and the epiphyses of the long bones.

Circulating CT levels are considered to be a marker for some types or stages of cancer, for example, medullary thyroid carcinoma, small-cell lung cancer, carcinoids, breast cancer, and gastrointestinal cancer. High affinity CT receptors have been identified in lymphoid cells, human lung cancer cell lines, human breast cancer cell lines, and in primary breast cancer tissue. Findlay et al. (1981) *Biochem. J.* 196: 513–520 reports that CT receptors are overexpressed in certain breast, lung, ovarian and lymphoma cancer cell lines.

The amino acid sequences of CT from several species (human, salmon and eel) are set forth below:

hCT    CGNLSTCMLGTYTQDFNKFHTFPQTAIGVG.A
         P.amide {SEQ ID NO.:1)

sCT    CSNLSTCVLGKLSQELHKLQTYPRTNTGSG.T
         P.amide (SEQ ID NO.:2)

eCT    CSNLSTCVLGKLSQELHKLQTYPRTDVGAGT
         P.amide (SEQ ID NO.:3)

(where single-letter abbreviations for amino acids can be found in Zubay, *Biochemistry* 2d ed., 1988, MacMillan Publishing: New York, p. 33, and where the underlined amino acids between the two cysteine residues in the amino terminal portion of the peptide represent a disulfide bond). Among species, nine residues, including the carboxyl-terminal proline amide and the disulfide-bonded cysteine residues at positions 1 and 7 are conserved. The salmon and eel CTs are more potent than human CT both in vitro and in vivo.

CT peptide analogs have been developed in which the chemically-labile disulfide is replaced with stable carbon-carbon linkages formed between 2-aminosuberic acid, as described in U.S. Pat. No. 4,086,221. CT analogs in which the amino terminal, midregion, or carboxyl terminal portion of the molecule are deleted demonstrate only weak binding to CT receptors. Many amino acid substitutions may be made between residues 8 and 22 of the CT molecule to generate biologically active CT analogs. Some CT analogs with only minimal sequence homology to any natural form of CT have biological activity similar to that of salmon CT. Truncated CT peptide derivatives (such as Cbz-LHKLQY-OMe, SEQ ID NO.: 12) also retain substantial receptor binding activity.

Since tumors may express or overexpress different receptors, a variety of radiodiagnostic and radiotherapeutic agents are needed to afford optimal diagnostic and therapeutic modalities against cancer.

SUMMARY OF THE INVENTION

CT receptors on cell surfaces of lung and ovarian adenocarcinoma, breast cancers and lymphomas can be exploited as markers to locate, identify, and treat such tumors in vivo. The present inventors have for the first time developed small, synthetic compounds, including CT-derived peptides, possessing the capacity for high-affinity binding to CT receptors and favorable pharmacokinetics, thereby permitting efficient in vivo localization of diagnostic and therapeutic agents at tumor sites. The reagents of the invention provide the basis of rapid, cost-effective, non-invasive diagnostic imaging procedures useful for tumor detection, disease staging and evaluation of metastatic spread of tumors characterized by expression or overexpression of CT receptors. The reagents of the invention also provide the basis for assessment of therapeutic effectiveness of other treatment modalities, for example, by localization of CT receptor-expressing tumor cells following surgery, radiation therapy or chemotherapy. The reagents of the invention may also be used as targeting moieties for site-directed radiotherapy.

The invention provides CT receptor binding reagents comprising CT receptor binding compounds, preferably CT peptides, CT derivatives, or CT analogues, which are covalently linked to a radiometal chelator. The CT receptor binding compounds employed in the reagents of the invention have a molecular weight of less than about 10,000 daltons. In some embodiments, the reagents of the invention are characterized as peptides, by virtue of the presence of a peptide linkage either in the CT receptor binding portion of the reagent or by virtue of the presence of a peptide linkage in the radiometal chelator. The reagents of the invention have a CT receptor binding affinity that is not less than about one-tenth the affinity of radioiodinated native CT for said receptor, when compared in a standardized assay such as the assays described in Example 4 below. In preferred embodiments, the reagents of the invention have a CT receptor binding affinity equal to or greater than native CT or radioiodinated species of native CT for said receptor, when compared in said standardized assay.

The radiopharmaceuticals of the invention may be employed as site specific diagnostic or therapeutic agents. When labeled with technetium-99m, iodine-123, and iodine-13 1, the reagents of the invention may be employed as scintigraphic imaging agents. When labeled with a magnetic, paramagnetic, supermagnetic, or superparamagnetic metal, the reagents of the invention may be employed as magnetic resonance contrast agents. When labeled with a cytotoxic radionuclides, the reagents of the invention may be used for site-directed radiotherapy. The invention also provides pharmaceutical compositions comprising the radiolabeled CT receptor-binding compounds of the invention and a pharmaceutically acceptable carrier. Methods for making the CT receptor binding reagents of the invention and radiolabeled embodiments thereof are also provided.

The invention also provides kits for preparing radiolabeled CT receptor binding compounds from the reagents of the invention. The kits of the invention comprise a sealed vial containing a predetermined quantity of a reagent of the invention and optionally a sufficient amount of a reducing agent to radiolabel the reagent.

This invention provides methods for using the radiolabeled CT receptor-binding reagents of the invention diagnostically and therapeutically. In one embodiment, methods are provided for using reagents of the invention, in labeled form, for imaging sites within a mammalian body by obtaining in vivo images. These methods comprise the steps of administering an effective diagnostic amount of labeled reagents of the invention and detecting the label localized at the site within the mammalian body.

The invention also provides methods for alleviating diseases characterized by expression or overexpression of CT receptors, comprising the step of administering a therapeutically effective amount of a radiolabeled CT receptor-binding reagents of the invention to the animal.

Other aspects and advantages of the present invention are apparent in the following more detailed description of preferred embodiments set forth below.

DETAILED DESCRIPTION OF THE INVENTION

The patent and scientific literature referenced herein establish the knowledge available to those with skill in the art. The issued U.S. patents and allowed applications are hereby incorporated by reference.

The present invention provides CT receptor binding reagents useful in the preparation of CT receptor binding pharmaceutical agents for diagnosis and therapy. For the purposes of this invention, the term "CT receptor binding compound" is intended to encompass naturally-occurring CT, fragments of CT, analogues of CT, and derivatives of CT that specifically bind to the CT receptor expressed in a variety of cell types recognized by those with skill in the art. Compounds designed to mimic the receptor-binding properties of CT are also included in this definition and encompassed by the invention.

For the purposes of this invention, the term "CT receptor binding affinity" is intended to mean binding affinity as measured by any methods known to those of skill in the art, including, inter alia, those methods which measure binding affinity by a dissociation constant, an inhibition constant or an $IC_{50}$ value.

The term "having a CT receptor binding affinity of at least one-tenth the affinity of radioiodinated CT for said receptor"

is intended to mean that the dissociation constant ($K_d$) of the reagent is not more than ten times the $K_d$ of radioiodinated CT as measured in a CT receptor direct binding or competitive inhibition assay, or that the or inhibition constant ($K_i$) or $IC_{50}$ of the reagent is not more than 10 times that of radioiodinated CT, as measured in a CT receptor competitive inhibition assay.

The term "having a CT receptor binding affinity equal to or greater than native CT or radioiodinated species of CT for said CT receptor" is intended to encompass reagents having a dissociation constant ($K_d$) equal to or less than that of unlabeled CT or radioiodinated CT, as measured in a CT receptor direct binding or competitive inhibition assay. Alternatively, this term may be interpreted as encompassing reagents having an inhibition constant ($K_i$) or $IC_{50}$ equal to or less than that of native CT or radioiodinated CT as measured in a CT receptor competitive inhibition assay.

In accordance with the invention, the reagents of the invention have a CT receptor binding affinity of at least ten times greater than the affinity of radioiodinated native CT for said receptor, when compared in a standardized assay as described below. In preferred embodiments, the reagents of the invention have a CT receptor binding affinity equal to or greater than native CT or radioiodinated species of native CT for said receptor, when compared in said standardized assay.

Dissociation constants or binding inhibition constants of the radiopharmaceuticals of the invention in relation to the CT receptor, as well as comparison of the affinity or avidity of such binding with binding of $^{125}$I-labeled CT itself, may be determined using known methods such as those set forth in *Receptors, A Quantitative Approach*, A. Levitzki, The Benjamin/Cummings Publishing Company (California, 1984). Preferably a standardized CT receptor binding assay, such as the assays set forth in Example 4 below, is employed to measure CT receptor binding affinity of the reagents of the invention.

In addition to the CT receptor binding compound, the reagents provided by this invention comprise a radiometal chelator which is covalently linked to the compound in such a way that the binding specificity of the compound for the CT receptor is not substantially altered. Any radiometal chelator may be covalently linked to a CT receptor binding compound to provide a reagent of the invention. For example, a CT receptor-binding compound, preferably a peptide, may be covalently linked to a chelator having the formula:

$$C(pgp)^s\text{-}(aa)\text{—}C(pgp)^s$$

where $(pgp)^s$ is hydrogen or a thiol protecting group and (aa) is any α- or β-amino acid not comprising a thiol group. In a preferred embodiment, the amino acid is glycine.

As another example, a radiometal chelator useful in the reagents of the invention comprises a single thiol-containing group of formula:

$$A\text{—}CZ(B)\text{—}\{C(R^aR^b)\}_n\text{—}X$$

wherein A is H, HOOC, $H_2NOC$, (peptide)-NHOC, (peptide)-OOC, $R^e{}_2NCo$, or $R^d$; B is H, SH or —$NHR^c$, —$N(R^c)$-(peptide) or $R^d$; Z is H or $R^d$; X is SH or —$NHR^c$, —$N(R^c)$-(peptide) or $R^d$; $R^a$, $R^b$, $R^c$ and $R^d$ are independently H or straight or branched chain or cyclic lower alkyl; n is 0, 1 or 2; $R^c$ is $C_1$–$C_4$ alkyl, an amino acid or a peptide comprising 2 to about 10 amino acids; and: (1) where B is —$NHR^c$ or —$N(R^c)$-(peptide), X is SH and n is 1 or 2; (2) where X is —$NHR^c$ or —$N(R^c)$-(peptide), B is SH and n is 1 or 2; (3) where B is H or $R^d$, A is HOOC, $H_2NOC$, (peptide)-NHOC, or (peptide)-OOC, X is SH and n is 0 or 1; (4) where A is H or $R^d$, then where B is SH, X is —$NHR^c$ or —$N(R^c)$-(peptide) and where X is SH, B is —$NHR^c$ or —$N(R^c)$-(peptide) and n is 1 or 2; (5) where X is H or $R^d$, A is HOOC, $H_2NOC$, (peptide)-NHOC, or (peptide)-OOC and B is SH; (6) where Z is methyl, X is methyl, A is HOOC, $H_2NOC$, (peptide)-NHOC, or (peptide)-OOC and B is SH and n is 0; and (7) where B is SH, X is not SH and where X is SH, B is not SH.

Preferred embodiments of this radiometal chelator have the chemical formula:

$$R^1\text{—Co-(amino acid)}^1\text{-(amino acid)}^2\text{—Z}$$

wherein (amino acid)$^1$ and (amino acid)$^2$ are each independently any primary α- or β-amino acid that does not comprise a thiol group, Z is a thiol-containing moiety that is cysteine, homocysteine, isocysteine, penicillamine, 2-mercaptoethylamine or 3-mercaptopropylamine, and $R^1$ is lower ($C^1$–$C^4$) alkyl, an amino acid or a peptide comprising 2 to 10 amino acids. When Z is cysteine, homocysteine, isocysteine or penicillamine, the carbonyl group of said moiety is covalently linked to a hydroxyl group, a $NR^3R^4$ group, wherein each of $R^3$ and $R^4$ are independently H or lower ($C^1$–$C^4$) alkyl, an amino acid or a peptide comprising 2 to 10 amino acids; or $$Y\text{-(amino acid)}^2\text{-(amino acid)}^1\text{-NHR}^2$$

wherein Y is a thiol-containing moiety that is cysteine, homocysteine, isocysteine, penicillamine, 2-mercaptoacetate or 3-mercaptopropionate, (amino acid)$^1$ and (amino acid)$^2$ are each independently any primary α- or β-amino acid that does not comprise a thiol group, and $R^2$ is H or lower ($C^1$–$C^4$) alkyl, an amino acid or a peptide comprising 2 to 10 amino acids. When Y is cysteine, homocysteine, isocysteine or penicillamine, the amino group of said moiety is covalently linked to —H, an amino acid or a peptide comprising 2 to 10 amino acids.

In particular embodiments of this aspect of the invention, the formula of this radiometal chelator is selected from the group consisting of:

-(amino acid)$^1$-(amino acid)$^2$—A—CZ(B)—{C($R^1R^2$)}$_n$—X },

—A—CZ(B)—{C($R^1R^2$)}$_n$—X}-(amino acid)$^1$-(amino acid)$^2$,

-(a primary α,ω- or β,ω-diamino acid)-(amino acid)$^1$—A—CZ(B)—{C($R^1R^2$)}$_n$—X}, and —A—CZ(B)—{C($R^1R^2$)})$_n$—X}-(amino acid)$^1$-(a primary α,β- or α,γ-diamino acid) wherein (amino acid)$^1$ and (amino acid)$^2$ are each independently any naturally-occurring, modified, substituted or altered α- or β-amino acid not containing a thiol group; A is H, HOOC, $H_2NOC$, (amino acid or peptide)-NHOC, (amino acid or peptide)-OOC or $R^4$; B is H, SH or —$NHR^3$, —$N(R^3)$-(amino acid or peptide) or $R^4$; Z is H or $R^4$; X is SH or —$NHR^3$, —$N(R^3)$-(amino acid or peptide) or $R^4$; $R^1$, $R^2$, $R^3$ and $R^4$ are independently H or straight or branched chain or cyclic lower alkyl; n is an integer that is either 0, 1 or 2; (peptide) is a peptide of 2 to about 10 amino acids; and: (1) where B is —$NHR^3$ or —$N(R^3)$-(amino acid or peptide), X is SH and n is 1 or 2; (2) where X is —$NHR^3$ or —$N(R^3)$-(amino acid or peptide), B is SH and n is 1 or 2; (3) where B is H or $R^4$, A is HOOC, $H_2NOC$, (amino acid or peptide)-NHOC, (amino acid or peptide)-OOC, X is SH and n is 0 or 1; (4) where A is H or $R^4$, then where B is SH, X is —$NHR^3$ or —$N(R^3)$-(amino acid or peptide) and where X is SH, B is —$NHR^3$ or —$N(R^3)$-(amino acid or peptide) and n is 1 or 2; (5) where X is H or $R^4$, A is HOOC, $H_2NOC$, (amino acid or peptide)-NHOC, (amino acid or peptide)-OOC and B is SH; (6) where Z is methyl, X is methyl, A is HOOC, $H_2NOC$, (amino acid or peptide)-NHOC, (amino acid or peptide)-OOC and B is SH and n is 0; and (7) where B is SH, X is not SH and where X is SH, B is not SH.

Specific preferred embodiments of this aspect of the invention include radiometal chelators having a formula selected from the group consisting of: -Gly-Gly-Cys-, Cys-Gly-Gly-, Gly-Gly-Cys-, -(ε-Lys)-Gly-Cys-, (δ-Orn)-Gly-Cys-, -(γ-Dab)-Gly-Cys-, -(β-Dap)-Lys-Cys-, and -(β-Dap)-Gly-Cys-. (In these formulae, it will be understood that ε-Lys represents a lysine residue in which the ε-amino group, rather than the typical α-amino group, is covalently linked to the carboxyl group of the adjacent amino acid to form a peptide bond; δ-Orn represents an ornithine residue in which the δ-amino group, rather than the typical α-amino group, is covalently linked to the carboxyl group of the adjacent amino acid to form a peptide bond; γ-Dab represents a 2,4-diaminobutyric acid residue in which the γ-amino group is covalently linked to the carboxyl group of the adjacent amino acid to form a peptide bond; and β-Dap represents a 1,3-diaminopropionic acid residue in which the β-amino group is covalently linked to the carboxyl group of the adjacent amino acid to form a peptide bond.)

In another embodiment, the radiometal chelator of the reagent of the invention is a bisamino-bisthiol chelator having the formula:

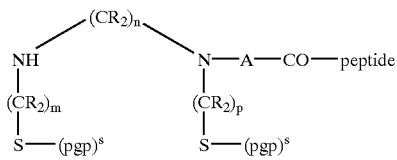

wherein each R can be independently H, $CH_3$ or $C_2H_5$; each $(pgp)^s$ can be independently a thiol protecting group or H; m, n and p are independently 2 or 3; A is linear or cyclic lower alkyl, aryl, heterocyclyl, combinations or substituted derivatives thereof; and X is peptide. Alternatively, the bisamino bisthiol chelator in this embodiment of the invention has the formula:

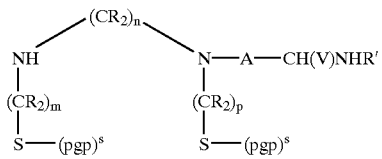

wherein each R is independently H, $CH_3$ or $C_2H_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is CO-peptide. For purposes of this invention, chelating moieties having these structures will be referred to as "BAT" moieties.

Alternatively, the radiometal chelator used in the reagent of the invention may have a formula selected from the group consisting of:

diethylenetriaminepentaacetic acid (DTPA)

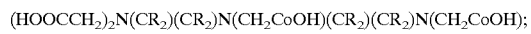

where each R is independently H, $C_1$ to $C_4$ alkyl, or aryl and one R is covalently linked to a bivalent linker;

ethylenediaminetetraacetic acid (EDTA)

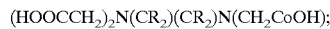

where each R is independently H, $C_1$ to $C_4$ alkyl, or aryl and one R is covalently linked to a bivalent linker;

1,4,7,10-tetraazadodecanetetraacetic acid;

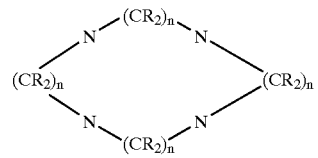

where n is an integer that is 2 or 3 and where each R is independently H, $C_1$ to $C_4$ alkyl, or aryl and one R is covalently linked to the CT receptor binding compound, and desferrioxamine.

Most radiometals may be chelated to reagents of the invention comprising the above-mentioned radiometal chelators.

The reagents of the invention may also comprise a radiometal chelator selected from the group consisting of:

(i) a group having the formula:

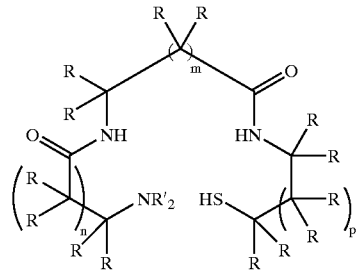

(ii) a group having the formula:

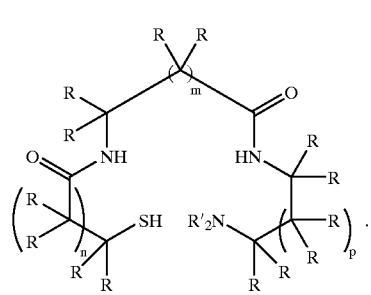

wherein n, m and p are each integers that are independently 0 or 1; each R' is independently H, lower alkyl, $C_2$–$C_4$ hydroxyalkyl, or $C_2$–$C_4$ alkoxyalkyl, and each R is independently H or R", where R" is substituted or unsubstituted lower alkyl or phenyl not comprising a thiol group, and one R or R' is L, where L is a bivalent linker moiety linking the metal chelator to the targeting moiety and wherein when one R' is L, $NR'_2$ is an amine.

In preferred embodiments, L is a $C_1$–$C_6$ linear, branched chain or cyclic alkyl group, a carboxylic ester, a carboxamide, a sulfonamide, an ether, a thioether, an amine, an alkene, an alkyne, a 1,2-, 1,3- or 1,4-linked, optionally substituted, benzene ring, or an amino acid or peptide of 2 to about 10 amino acids, or combinations thereof.

In preferred embodiments, R" is a $C_1$–$C_6$ linear, branched or cyclic alkyl group; a —$C_qOC_r$—, —$C_qNHC_r$— or —$C_qSC_r$— group, where q and r are integers each independently 1 to 5 wherein the sum of q+r is not greater than 6; ($C_1$–$C_6$) alkyl-X, where X is a hydroxyl group, a substituted amine, a guanidine, an amidine, a substituted thiol group, or a carboxylic acid, ester, phosphate, or sulfate group; a phenyl group or a phenyl group substituted with a halogen, hydroxyl, substituted amine, guanidine, amidine, substituted thiol, ether, phosphate, or sulfate group; an indole group; a $C_1$–$C_6$ heterocyclic group containing 1 to 3 nitrogen, oxygen or sulfur atoms or combinations thereof.

In accordance with the invention, the radiometal chelator of the CT receptor-binding reagent may have the formula:

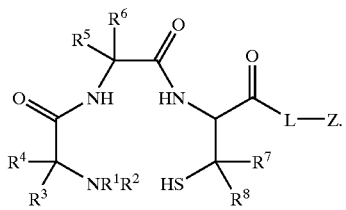

III wherein $R^1$ and $R^2$ are each independently H, lower alkyl, $C_2$–$C_4$ hydroxyalkyl, or $C_2$–$C_4$ alkoxyalkyl; $R^3$, $R^4$, $R^5$ and $R^6$ are independently H, substituted or unsubstituted lower alkyl or phenyl not comprising a thiol group; $R^7$ and $R^8$ are each independently H, lower alkyl, lower hydroxyalkyl or lower alkoxyalkyl; L is a bivalent linker group and Z is a CT peptide.

Additional preferred metal chelators of the invention include chelators of formula:

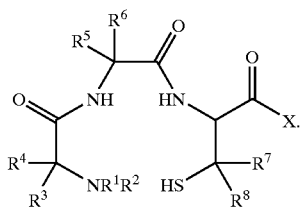

IV wherein $R^1$ and $R^2$ are each independently H, lower alkyl, $C_2$–$C_4$ hydroxyalkyl, or $C_2$–$C_4$ alkoxyalkyl; $R^3$, $R^4$, $R^5$ and $R^6$ are independently H, substituted or unsubstituted lower alkyl or phenyl not comprising a thiol group, and one of $R^3$, $R^4$, $R^5$ or $R^6$ is Z—L—HN($CH_2$)$_n$—, where L is a bivalent linker group, Z is a targeting moiety, and n is an integer from 1 to 6; $R^7$ and $R^8$ are each independently H, lower alkyl, lower hydroxyalkyl or lower alkoxyalkyl; and X is an amino group, a substituted amino group or —$NR^1$-Y, where Y is an amino acid, an amino acid amide, or a peptide comprising from 2 to 10 amino acids.

More preferred metal chelators of the invention include chelators having the formula:

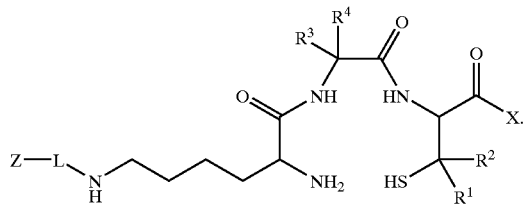

V wherein $R^1$ and $R^2$ are each independently H, lower alkyl, lower hydroxyalkyl, or lower alkenylalkyl; $R^3$ and $R^4$ are independently H, substituted or unsubstituted lower alkyl or phenyl not comprising a thiol group; n is an integer from 1 to 6; L is a bivalent linker group; and Z is a CT peptide moiety.

Additional more preferred chelating moieties include chelators of formula:

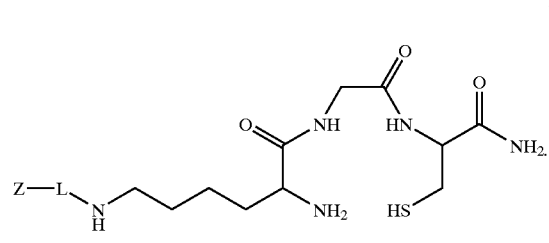

VI wherein L is a bivalent linker group and Z is a CT peptide moiety.

Most preferred chelating moieties of the invention include chelators having the following formulae:

(amino acid)$^1$-(amino acid)$^2$-cysteine-,
(amino acid)$^1$-(amino acid)$^2$-isocysteine-,
(amino acid)$^1$-(amino acid)$^2$-homocysteine-,
(amino acid)$^1$-(amino acid)$^2$-penicillamine-,
(amino acid)$^1$-(amino acid)$^2$-2-mercaptoethylamine-,
(amino acid)$^1$-(amino acid)$^2$-2-mercaptopropylamine-,
(amino acid)$^1$-(amino acid)$^2$-2-mercapto-2-methylpropylamine-,
(amino acid)$^1$-(amino acid)$^2$-3-mercaptopropylamine-,
wherein (amino acid) in a primary α- or β-amino acid not comprising a thiol group and wherein the chelator is attached to either a targeting moiety or a linker group via a covalent bond with the carboxyl terminus of the chelator or a side chain on one of the amino acid groups.

Most preferred chelators also include chelators of the above formula wherein (amino acid)$^1$ is either an α,ω- or β,ω-amino acid wherein the α- or β-amino group is a free amine and the α,ω- or β,ω-amino acid is covalently linked via the ω amino group.

Other most preferred chelators include those selected from the group consisting of:

-cysteine-(amino acid)-(α,β- or β,γ-diamino acid);
-isocysteine-(amino acid)-(α,β- or β,γ-diamino acid);
-homocysteine-(amino acid)-(α,β- or β,γ-diamino acid);
-penicillamine-(amino acid)-(α,β- or β,γ-diamino acid);
2- mercaptoacetic acid-(amino acid)-(α,β- or β,γ-diamino acid);
2- or 3-mercaptopropionic acid-(amino acid)-(α,β- or β,γ-diamino acid);
2-mercapto-2-methylpropionic acid-(amino acid)-(α,β- or β,γ-diamino acid);

wherein (amino acid) in a primary α- or β-amino acid not comprising a thiol group and wherein the chelator is attached to either a targeting moiety or a linker group via a covalent bond with the amino terminus of the chelator or a side chain on one of the amino acid groups.

Particularly preferred metal chelators are selected from the group consisting of: Gly-Gly-Cys-, Arg-Gly-Cys-, -(ε-Lys)-Gly-Cys-, -(δ-Orn)-Gly-Cys-, -(γ-Dab)-Gly-Cys-, -(β-Dap)-Lys-Cys-. and -(β-Dap)-Gly-Cys-. (In these formulae, the amino acid designations have the same meaning as is set forth above.)

An example of a radiometal chelator having structure III above is Gly-Gly-Cys-, wherein the chelating moiety has the structure:

VII

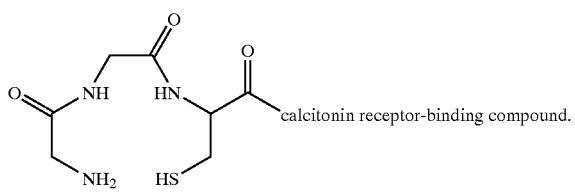

Chelating ligands having structure type VII form oxotechnetium complexes having the structure:

VIII

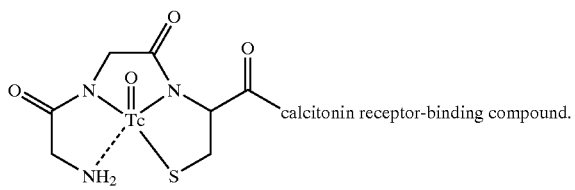

An example of radiometal chelators having structure type V as shown above is Lys-(ω-peptide)-Gly-Cys.amide which forms a chelator of structure:

IX

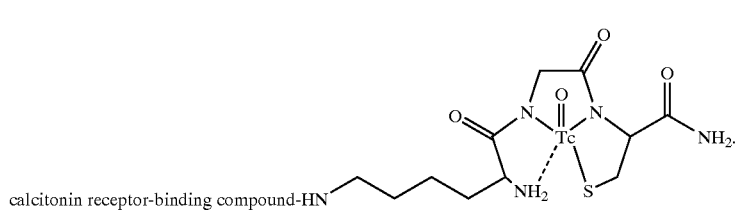

Chelating ligands having structure type IX form oxotechnetium complexes having the structure:

X

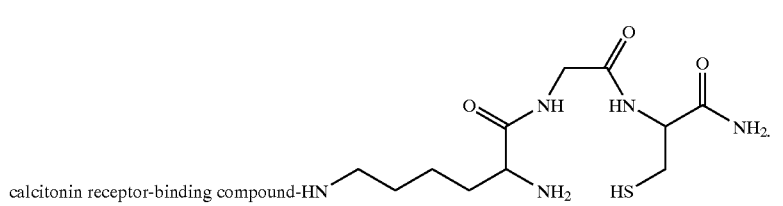

An example of a reagent of the invention comprising a radiometal chelator having structure II as shown above is (targeting moiety)-Cys-Gly-α,β-diaminopropionamide which forms a chelator of structure:

XI

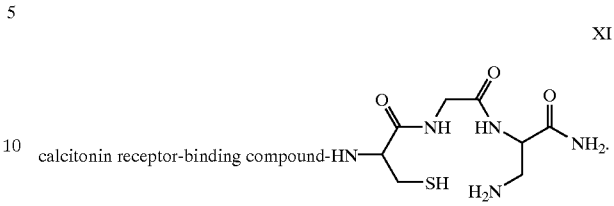

Radiodiagnostic agents having structure type XI form oxotechnetium complexes having the structure:

XII

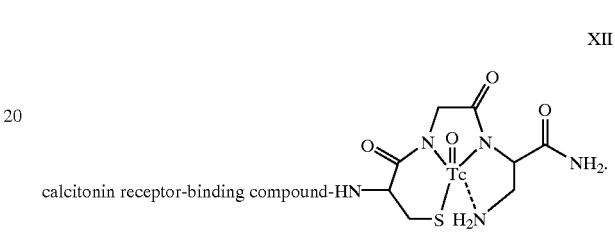

In the radiometal chelators and CT receptor binding reagents provided by the invention that contain a thiol covalently linked to a thiol protecting group {(pgp)$^S$}, the thiol-protecting groups may be the same or different and may be but are not limited to:

—$CH_2$-aryl (aryl is phenyl or alkyl or alkyloxy substituted phenyl);
—CH-(aryl)$_2$, (aryl is phenyl or alkyl or alkyloxy substituted phenyl);
—C-(aryl)$_3$, (aryl is phenyl or alkyl or alkyloxy substituted phenyl);
—$CH_2$-(4-methoxyphenyl);
—CH-(4-pyridyl)(phenyl)$_2$;
—C(CH$_3$)$_3$
-9-phenylfluorenyl;

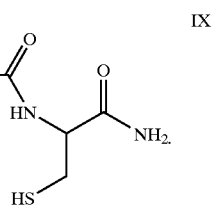

—$CH_2$NHCoR (R is unsubstituted or substituted alkyl or aryl);

—$CH_2$—NHCoOR (R is unsubstituted or substituted alkyl or aryl);
—CoNHR (R is unsubstituted or substituted alkyl or aryl);
—$CH_2$—S—$CH_2$-phenyl Preferred protecting groups have the formula —$CH_2$—NHCoR wherein R is a lower alkyl having between 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

When the reagent of the of the invention comprises a CT receptor binding compound which is a peptide, the peptide preferably comprises the amino acid sequence:

$CH_2$Co.SNLSTX— (SEQ ID NO.:10)

wherein X is selected from the group consisting of a cysteine residue, a homocysteine residue, and a homohomocysteine residue. Alternatively, the peptide may comprise the amino acid sequence:

$CH_2$Co.$X^1$NLST$X^2$— (SEQ ID NO.:11)

wherein $X^1$ is selected from the group consisting of an alanine residue, a glycine residue, and a serine residue; and $X^2$ is selected from the group consisting of a cysteine residue, a homocysteine residue, and a homohomocysteine residue. Such peptides include naturally-occurring human CT and CT peptide analogs such as those which are specifically embodied in the amino acid sequences set forth below:
$CH_2$CO.SNLST.Hhc.VLGKLSCELHKLQTYPRTNTGS GTP.amide; (SEQ ID NO.:5) $CH_2$CO.SNLST.Hcy.VLGKLSCELHKLQTYPRTNTGS GTP.amide; (SEQ ID No.:6) $CH_2$CO.SNLST.Cys.VLGKLSCELHKLQTYPRTNTGS GTP.amide; (SEQ ID NO.:7) and SNLST.Asu.V-LGKLSCELHKLQTYPRTNTGSGTP.amide (SEQ ID NO.:8)

Particularly preferred embodiments of the reagents of the invention include: $CH_2$CO.SNLST.Hhc.VLGKLSC(BAT)ELHKLQTYPRTNTGSGTP.amide (SEQ ID NO.:4) $CH_2$CO.SNLST.Hhc.VLGKLSQELHKLQTYPRTNTGS GTP($\epsilon$-K)GC.amide, (SEQ ID NO.:13) $CH_2$CO.SNLST.Hhc.VLGKLSC($CH_2$CO.GGCK.amide)ELHKLQTYPRTNTGSGTP.amide, (SEQ ID NO.:14) $CH_2$CO.SNLST.Hhc.VLGKLSC($Ch_2$CO.($\beta$-Dap)KCK.amide)ELHKLQTYPRTNTGSGTP.amide, (SEQ ID NO.:15) $CH_2$CO.SNLST.Hhc.VLGKLSC($CH_2$CO.($\epsilon$-K)GCE.amide)ELHKLQTYPRTNTGSGTP.amide, (SEQ ID NO.:16) $CH_2$CO.SNLST.Hcy.VLGKLSC($CH_2$CO.GGCK.amide)ELHKLQTYPRTNTGSGTP.amide, (SEQ ID NO.:17) $CH_2$CO.SNLST.Hcy.VLGKLSC($CH_2$CO.($\beta$-Dap)KCK.amide)ELHKLQTYPRTNTGSGTP.amide, (SEQ ID NO.:18) $CH_2$CO.SNLST.Hcy.VLGKLSC($CH_2$CO.($\epsilon$-K)GCE.amide)ELHKLQTYPRTNTGSGTP.amide, (SEQ ID NO.:19) $CH_2$CO.SNLST.Cys.VLGKLSC($CH_2$CO.GGCK.amide)ELHKLQTYPRTNTGSGTP.amide, (SEQ ID NO.:20) $CH_2$CO.SNLST.Cys.VLGKLSC($CH_2$CO.($\beta$-Dap)KCK.amide)ELHKLQTYPRTNTGSGTP.amide, (SEQ ID NO.:21) $CH_2$CO.SNLST.Cys.VLGKLSC($CH_2$CO.($\epsilon$-K)GCE.amide)ELHKLQTYPRTNTGSGTP.amide, (SEQ ID NO.:22) SNLST.Asu.VLGKLSC($CH_2$CO.($\beta$-Dap)KCK.amide)ELHKLQTYPRTNTGSGTP.amide, (SEQ ID NO.:23)and SNLST.Asu.VLGKLSC($CH_2$CO.($\beta$-Dap)KCK.amide)ELHKLQTYPRTDVGAGTP.amide, (SEQ ID NO.:24).

All naturally-occurring amino acids are abbreviated using standard abbreviations (which can be found in G. Zubay, *Biochemistry* (2d. ed.), 1988 (MacMillen Publishing: New York) p.33). For the purposes of this invention, the naturally-occurring amino acids are characterized as lipophilic (alanine, isoleucine, leucine, methionine, phenylalanine, tyrosine, proline, tryptophan and valine, as well as S-alkylated derivatives of cysteine), hydrophilic (asparagine, glutamine, threonine, serine), acidic (glutamic acid and aspartic acid), basic (arginine, histidine and lysine). $\epsilon$-K, $\delta$-Orn, $\gamma$-Dab and $\beta$-Dap have the meanings set forth above. (BAT) represents $N^6,N^9$-bis(2-mercapto-2-methylpropyl)-6,9-diazanonanoic acid; K.(BAT) and Lys.(BAT) represent the amino acid lysine, acylated at the $\epsilon$-amino group on the amino acid sidechain to (BAT); C(BAT) and Cys(BAT) represent S-($N^6,N^9$-bis(2-mercapto-2methylpropyl)-6,9--diazanonan-1-yl)cysteine; (BAM) is ($N^1,N^4$-bis(2-mercapto-2-methylpropyl)-1,4,10-triazadecane; (BAT-BM) is N-{2-(N',N'-bis(2-maleimidoethyl)aminoethyl}-$N^9$-(t-butoxycarbonyl)-$N^6$, $N^9$-bis(2-methyl-2-triphenylmethylthiopropyl)-6,9-diazanonanamide; (BAT-BS) is N-{2-(N',N'-bis(2-succinimidoethyl)aminoethyl)-$N^6,N^9$-bis(2-mercapto-2-methylpropyl)-6,9-diazanonanamide; (BMH) is bis-maleimidohexane; (BSH) is bis-succinimidohexane; (BMME) is bis-maleimidomethylether; (BSEE) is bis-succinimidoethylether; (BMEE) is bis-maleimidoethylether; and (BSME) is bis-succinimidomethylether. As used herein, the following amino acids and amino acid analogues are intended to be represented by the following abbreviations: Acm is the sulfhydryl protecting group acetamidomethyl; Pen is penicillarnine; Aca is 6-aminocaproic acid; Hly is homolysine; Apc is L-{S-(3-aminopropyl)cysteine; $F_D$ is D-phenylalanine; $W_D$ is D-tryptophan; $Y_D$ is D-tyrosine; Cpa is L-(4-chlorophenyl)alanine; Thp is 4-amino-tetrahydrothiopyran-4-carboxylic acid; D-Nal is D-2-naphthylalanine; Dpg is dipropylglycine; Nle is norleucine; Hcy is homocysteine; Hhc is homohomocysteine; Aib is aminoisobutyric acid; Nal is 2-naphthylalanine; D—Nal is D-2-naphthylalanine; Ain is 2-aminoindan-2-carboxylic acid; Achxa is 4-amino-cyclohexylalanine; Amf is 4-aminomethyl-phenylalanine; Aec is S-(2-aminoethyl)cysteine; Apc is S-(3-aminopropyl)cysteine; Aes is O-(2-aminoethyl)serine; Aps is O-(3-aminopropyl)serine; Abu is 2-aminobutyric acid; Nva is norvaline; and Asu is 2-amino suberic acid, wherein the amino terminal amino acids of peptides containing an Asu residue are cyclized via an amide bond between the amino terminal amino group and the side chain carboxylic acid moiety of the Asu residue.

In accordance with the invention, CT receptor binding peptides may comprise one or more amino acid derivatives having a radiometal chelator linked to an amino acid sidechain. Preferably, the radiometal chelator is incorporated into the peptide at the carboxyl terminus of the CT receptor binding peptide. More preferably, the radiometal chelator is incorporated into the synthetic, CT receptor binding peptide at the sidechain sulfur atom of a cysteine corresponding to position 14 of the native peptide. Most preferably, the radiometal chelator is incorporated into a sidechain of an amino acid of the CT receptor binding peptide having the sequence $CH_2$CO.SNLST.Hhc.VLGKLSCELHKLQTYPRTNTGSGTP.amide. (SEQ ID NO.:9)

Most preferably, the radiometal chelator is incorporated into the CT receptor binding peptide at the sidechain sulfur atom of the cysteine at position 13 of the peptide depicted above (distinguished by the bold highlighting in said peptide).

Additional embodiments of the reagents of the invention comprise at least two synthetic CT receptor binding compounds, each compound being covalently linked to a radiometal chelator, and a polyvalent linker forming a covalent linkage selected from the group consisting of a linkage to each compound, a linkage to each chelator, and a linkage to one compound and to the chelator of the other compound. Additional permutations of this embodiment may also occur, in accordance with the invention. Polyvalent linkers suitable for use in this embodiment of the invention comprise at least two identical functional groups capable of covalently bonding to CT analogues, CT receptor binding compounds, CT peptides or radiometal chelators, or capable of binding both to a CT receptor binding compound and to a radiometal chelator. Preferred functional groups include, without limitation, primary amines, secondary amines, hydroxyl groups, carboxylic acid groups or thiol-reactive groups. In preferred embodiments, the polyvalent linkers comprise bis-succinimidylmethylether (BSME), bis-succinimidylethylether (BSEE), 4-(2,2-dimethylacetyl) benzoic acid (DMBA), N-{2-(N',N'-bis(2-succinimido-ethyl)aminoethyl)}-$N^6$,$N^9$-bis(2-methyl-2-mercapto-propyl)-6,9-diazanonanamide (BAT-BS), tris (succinimidylethyl)amine (TSEA), bis-succinimidohexane (BSH), 4-(O-$CH_2$Co-Gly-Gly-Cys.amide)-2-methylpropiophenone (ETAC), tris(acetamidoethyl)amine, bis-acetamidomethyl ether, bis-acetamidoethyl ether, α,ε-bis-acetyllysine, lysine and 1,8-bis-acetamido-3,6-dioxa-octane, or derivatives thereof.

CT receptor binding compounds provided by the present invention can be chemically synthesized in vitro using any suitable synthetic method. Preferably, CT peptides may be synthesized in accordance with the invention using recombinant methods. More preferably, CT peptides, CT peptide derivatives, and CT peptide analogues can generally advantageously be prepared in accordance with the present invention using a peptide synthesizer. The CT peptides of this invention are preferably synthesized by covalently linking the radiometal chelator to the peptide during chemical synthesis in vitro, using techniques well known to those with skill in the art such as solid phase peptide synthesis. In this manner, radiometal chelators may be incorporated into the peptide in a site-selective fashion at virtually any position in the peptide thereby avoiding a decrease in the affinity and specificity of the peptide for the CT receptor.

In accordance with the invention, CT receptor binding peptides are prepared having a protected thiol-containing amino acid, typically a cysteine residue, incorporated into the peptide. Following cleavage of the peptide from the synthetic resin and cyclization of the amino terminal residues, the protected thiol group is deprotected and elaborated with a prosthetic group containing a radiometal chelator and a thiol-reactive group.

As set forth above, the CT receptor binding reagents of the invention are capable of being radiolabeled to provide radiodiagnostic or radiotherapeutic agents. An exemplary radiodiagnostic application using the radiolabeled reagents of the invention is scintigraphic imaging, wherein the location and extent of CT receptor-bearing tumors may be determined. The term "scintigraphic imaging agent" as used herein is meant to encompass a radiolabeled reagent capable of being detected with a radioactivity detecting means (including but not limited to a gamma-camera or a scintillation detector probe). In the radiotherapeutic embodiments of the invention, CT receptor binding reagents are labeled with a cytotoxic radionuclides and are useful in the treatment of diseases or other ailments in animals, preferably humans, such diseases or ailments being characterized by expression or overexpression of CT receptors. CT-related diseases or ailments include but are not limited to breast cancer, ovarian cancer, lung cancer, lymphoma and other diseases characterized by the growth of malignant or benign tumors capable of binding CT receptor binding compounds, CT or derivatives or analogues thereof via the expression of CT receptors on the cell surface of cells comprising such tumors.

Any radiometal may be complexed with the reagents of the invention to provide a radiodiagnostic or radiotherapeutic agent. For example, the reagents of the invention may be radiolabeled with technetium-99m, iodine-125, or iodine-123 to provide a scintigraphic imaging agent. This invention also provides CT receptor-binding reagents capable of forming a complex with a magnetic, paramagnetic, supermagnetic, or superparamagnetic metal atom, ion or particle. The CT receptor binding reagents of the invention can also advantageously be radiolabeled with a cytotoxic radioisotope selected from the group consisting of scandium-47, copper-67, gallium-72, yttrium-90, tin-117m, iodine-125, iodine-131, samarium-153, gadolinium-159, dysprosium-165, holmium-166, ytterbium-175, lutetium-177, rhenium-186, rhenium-188, astatine-211, bismuth-212, and bismuth-213 to provide a radiotherapeutic agent.

When the reagents of the invention are used to form a complex of radioactive technetium or rhenium, the technetium complex, preferably a salt of technetium-99m pertechnetate, or rhenium in the form of perrhenate, is reacted with the reagent in the presence of a reducing agent. Preferred reducing agents are dithionite, stannous and ferrous ions; the most preferred reducing agent is stannous chloride. Alternatively, the complex may be formed by reacting a reagent of this invention with a pre-formed labile complex of technetium or rhenium and another compound known as a transfer ligand. This process is known as ligand exchange and is well known to those skilled in the art. The labile complex may be formed using such transfer ligands as tartrate, citrate, gluconate or mannitol, for example. Among the technetium-99m pertechnetate and rhenium salts useful with the present invention are included the alkali metal salts such as the sodium salt, or ammonium salts or lower alkyl ammonium salts.

The invention is also embodied in a kit for preparing radiometal-labeled reagents for use as radiopharmaceuticals. The kit of the invention comprises a sealed vial containing a predetermined quantity of the CT receptor binding reagent, and optionally, when the radiometal is technetium-99m, rhenium-186, or rhenium-188, a reducing agent. For example, an appropriate quantity of a reagent of the invention is introduced into a vial containing a reducing agent, such as stannous chloride, in an amount sufficient to label the reagent with technetium-99m, rhenium-186 or rhenium-188. An appropriate amount of a transfer ligand as described (such as tartrate, citrate, gluconate, glucoheptanate or mannitol, for example) can also be included in the kit. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form. Technetium-99m, rhenium-186 and rhenium-188 labeled radiopharmaceuticals according to the present invention may be prepared by the addition of an appropriate amount of technetium-99m, rhenium-186 or rhenium-188, or radionuclide complexes thereof, into the vials and reaction under conditions described in the Examples below.

The kit of the invention may be embodied in a form suitable for diagnostic imaging or as a therapeutic agent using a radioisotope of iodine, including iodine-123 and iodine-131, and preferably iodine-123. In this embodiment, the kit comprises a sealed vial containing a predetermined quantity of a CT receptor binding reagent capable of being radiolabeled with an iodine isotope. CT receptor binding reagents suitable for use in this embodiment include CT itself, a CT derivative, a CT analogue, CT mimetics and CT peptidomimetics that specifically bind to the CT receptor. When peptide and peptidomimetic CT receptor binding reagents are employed in this embodiment, a tyrosine residue in the reagent may be radioiodinated. Such a tyrosine residue may occur naturally in the peptide or peptidomimetic, or the tyrosine residue may be added at a position in the peptide or peptidomimetic that does not disrupt binding of the reagent to CT receptors. Dose, sites and routes of administration, formulations and administered specific radioactivity using the kit of this embodiment are as described herein for technetium and rhenium-labeled reagents for scintigraphic and therapeutic uses.

The imaging agents provided by the invention have utility for tumor imaging, particularly for imaging primary and metastatic neoplastic sites characterized by neoplastic cells that express or overexpress CT receptors, and in particular such primary and especially metastatic breast, lung and ovarian tumor-derived cells that have been clinically recalcitrant to detection using conventional methodologies. The imaging reagents provided by the present invention can also be used for visualizing organs such as the kidney or bone for diagnosing disorders in these organs.

For diagnostic purposes, an effective diagnostic amount of the diagnostic or radiodiagnostic agent of the invention is administered, preferably intravenously. In radiodiagnostic embodiments, localization of the radiolabel is detected using conventional methodologies such as gamma scintigraphy. In non-radioactive diagnostic embodiments, localization of sites of accumulation of the paramagnetic metal4abeled diagnostic agents of the invention is achieved using magnetic resonance imaging methodologies.

In accordance with this invention, for scintigraphic imaging the technetium-99m labeled reagents of the invention are administered in a single unit injectable dose. The technetium-99m labeled reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging in vivo can take place in a matter of a few minutes. However, imaging can take place, if desired, in hours or even longer, after the radiolabeled reagent is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

For the purposes of this invention, radiotherapy encompasses any therapeutic effect ranging from pain palliation to tumor ablation or remission of symptoms associated with the particular cancer being treated. When the reagents of the invention are used for therapeutic purposes, they are radiolabeled with an effective amount of a cytotoxic radioisotope. For this purpose, an amount of cytotoxic radioisotope from about 10 mCi to about 200 mCi may be administered via any suitable clinical route, preferably by intravenous injection.

In accordance with this invention, effective radiodiagnostic and radiotherapeutic agents may be identified as follows. Reagents of the invention comprising CT receptor binding compounds, including CT fragments, CT peptide analogues and CT derivatives, are synthesized using the methods of the invention and a radiometal chelator is covalently linked to the compound. The reagents are then complexed with a radiometal or a non-radioactive isotope having chelation characteristics similar to the desired radiometal, and CT receptor binding is then evaluated in in vitro competition binding assays as described herein using radioiodinated CT. As an example of this methodology, ReO is employed to evaluate the suitability of CT receptor-binding peptides for use as 99m-technetium radiolabeled scintigraphic imaging agents, as disclosed in Example 4 below.

The methods for making and labeling these compounds are more fully illustrated in the following Examples, which illustrate certain aspects of the above-described invention and advantageous results and are shown by way of illustration and not limitation.

EXAMPLE 1

Synthesis of BAT Chelators

BAT chelators, in particular S-cysteine derived and ε-amino Lysine derived BAT chelators, are prepared according to the methods of co-owned and co-pending U.S. Ser. No. 08/414,424, incorporated by reference herein.

EXAMPLE 2

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTU/HOBT), and using p-hydroxymethyl phenoxymethyl-polystyrene (HMP) resin or Sasrin™ or chlorotrityl resin for carboxyl-terminus acids or Rink amide resin for carboxyl-terminus amides.

Where appropriate, Fmoc-Cys(BAT) and Nα-Fmoc-Nε-(BAT)Lys were synthesized as described in co-owned and co-pending U.S. Ser. No. 08/414,424, incorporated by reference herein.

Where appropriate, 2-chloroacetyl, 2-bromoacetyl and 2-bromo-3-phenylpropionyl groups are introduced either by using the appropriate 2-halo acid as the last residue coupled during SPPS, or by treating the N-terminus free amino acid peptide bound to the resin with either 2-halo acid/diisopropylcarbodiimide/N-hydroxysuccinirnide/NMP or 2-halo acid anhydride/diisopropylethylamine/NMP.

Where appropriate, HPLC-purified 2-haloacylated peptides are cyclized by stirring an 0.1–1.0 mg/mL solution in phosphate or bicarbonate buffer or dilute ammonium hydroxide (pH 8.0), optionally containing 0.5–1.0 mM EDTA, or acetonitrile or THF for 1–48 h followed optionally by acidification with acetic acid, lyophilization and HPLC purification.

Where appropriate, thiol-containing peptides are reacted with chloroacetyl-containing, thiol-protected Technetium-99m complexing moieties at pH 10 for 0.5–4 hours at room temperature, followed by acetic acid acidification and evaporation of the solution to give the corresponding peptide-sulfide adduct. Deprotection and purification are routinely performed as described to yield the chelator-peptide conjugate.

Where appropriate, BSME, BSEE and BSH adducts are prepared by reacting single thiol-containing peptides (5 to 50 mg/mL in DMF buffered to pH 7 with N-methylmorpholine or N-ethyl-morpholine, or 50 mM sodium phosphate buffer, pH 7–8, optionally containing 0.5 mM EDTA or DMF or THF or acetonitrile) with 0.5 molar equivalents of BMME (bis-maleimidomethylether), BMEE (bis-maleimidoethylether) or BMH (bis-maleimidohexane), respectively, pre-dissolved in acetonitrile at room temperature for approximately 1–18 hours. The solution was concentrated and the product was purified by HPLC.

Where appropriate, TSEA adducts are prepared by reacting single thiol-containing peptide (at concentrations of 10 to 100 mg/mL peptide in DMF buffered to pH 7 with N-methylmorpholine or N-ethylmorpholine, or 5 to 50 mg/mL peptide in 50 mM sodium phosphate, pH 7–8, optionally containing 0.5 mM EDTA or DMF or THF or acetonitrile) with 0.33 molar equivalents of TMEA (tris(2-maleimidoethyl)amine) pre-dissolved in acetonitrile or DMF, with or without 1 molar equivalent of triethanolamine, at room temperature for approximately 1–18 h. Such reaction mixtures containing adducts are concentrated and the adducts are then purified using HPLC.

Where appropriate, (BAM) ($N^1,N^4$-bis(2-mercapto-2-methylpropyl)-1,4,10-triazadecane) is conjugated to the peptide by first activating the peptide carboxylate with a mixture of diisopropylcarbodiimide/ N-hydroxysuccinimide or HBTU/HOBt in DMF, NMP or methylene chloride, followed by coupling in the presence of diisopropylethylamine. After coupling, the conjugates are deprotected as described above.

Where appropriate, (BAT) ($N^6,N^9$-bis(2-mercapto-2-methylpropyl)-6,9-diazanonanoic acid) is incorporated into peptides as protected amino acid derivatives, such as (Nα(Fmoc)-Nε(N-Boc)-S,S'-bistrityl-BAT)lysine (prepared from Nα(Fmoc)-lysine and Nε(N-Boc)-S,S'-bistrityl-BAT as described in Example 2 of co-owned and co-pending U.S. patent application Ser. No. 08/044,825, incorporated by reference), or as (N(Fmoc)-S,S'-bistrityl-BAT)cysteine (prepared as described in Example 1F of co-owned and copending U.S. Ser. No.8/414,424, incorporated by reference) during peptide synthesis and then deprotected after cleavage of the completed peptide from the synthetic resin.

Where appropriate, BAT-BS (N-{2-(N',N'-bis(2-succinimidoethyl) aminoethyl)}-$N^6,N^9$-bis(2-methyl-2-mercaptopropyl)-6,9-diazanonanamide) adducts are prepared by reacting single thiol-containing peptide (at concentrations of 2 to 50 mg/mL peptide in DMF buffered to pH 7 with N-methylmorpholine or N-ethylmorpholine, or in 50 mM sodium phosphate (pH 7–8), optionally containing 0.5 mM EDTA or DMF or THF or acetonitrile) with 0.5 molar equivalents of BAT-BM (N-{2-(N',N'-bis(2-maleimidoethyl)aminoethyl)}-$N^9$-(t-butoxycarbonyl)-$N^6$, $N^9$-bis(2-methyl-2-triphenylmethylthiopropyl)-6,9-diazanonanamide) pre-dissolved in acetonitrile or THF, at room temperature for approximately 1–18 h. The solution is then evaporated to dryness and (3AT-BS)-peptide conjugates deprotected by treatment with 10 mL TFA and 0.2 mL triethylsilane for 1 h. The solution is concentrated, the product adducts precipitated with ether, and then purified by HPLC.

Where appropriate, peptide precursors are cyclized (between the amino- and carboxyl-termini) by reaction of the sidechain-protected, N-terminal free amine and C-terminal free acid with diphenylphosphorylazide.

Sasrin™ resin-bound peptides are cleaved using a solution of 1% TFA in dichloromethane to yield the protected peptide. Where appropriate, protected peptide precursors are cyclized between the amino- and carboxyl-termini by reaction of sidechain-protected, amino-terminal free amine and carboxyl-terminal free acid using diphenylphosphorylazide.

HMP or Rink amide resin-bound products are routinely cleaved and protected cyclized peptides deprotected using a solution comprised of trifluoroacetic acid (TFA), or TFA and methylene chloride, optionally comprising water, thioanisole, ethanedithiol, and triethylsilane or triisopropylsilane in ratios of 100:5:5:2.5:2, for 0.5–3 hours at room temperature. Where appropriate, products were re-S-tritylated in triphenolmethanol/TFA, and N-Boc groups re-introduced into the peptide using (Boc)$_2$O.

Where appropriate, thiol functionalities within the peptide or peptidometic sequence designed for further elaboration with a prosthetic group were protected using compound such as S-t-butyl (to produce mixed t-butyl disulfides) or p-methoxybenzyl. S-t-butyl groups are removed by treatment with a solution of dithiothreitol or mercaptoethanol, while p-methoxybenzyl groups are removed using boron trifluoride etherate in trifluoroacetic acid in the presence of a free radical scavenger such as m-cresol. Prosthetic peptides containing radiometal binding moieties are prepared by SPPS ending with an N-terminal 2-haloacetyl group. The prosthetic group are removed from the resin and any thiol groups are-protected, for example, with a trityl group. The haloacetylated sequence is then coupled with the thiol-containing peptide under essentially the same conditions as described above for preparing cyclic thioethers. Removal of remaining protecting groups is then achieved using the methods described herein to yield the final product.

Crude peptides are purified by preparative high pressure liquid chromatography (HPLC) using a Waters Delta Pak C18 column and gradient elution using 0.1% trifluoroacetic acid (TFA) in water modified with acetonitrile. Acetonitrile is evaporated from the eluted fractions which are then lyophilized. The identity of each product is confirmed by fast atom bombardment mass spectroscopy (FABMS) or by electrospray mass spectroscopy (ESMS).

CT receptor binding peptides, derivatives and analogues synthesized as provided herein, as well as the products of such synthesis identified by ESMS or FABMS, are shown in Table I below.

TABLE I

| Peptide | Peptide | ReO Complex |
|---|---|---|
| 1. CH₃CO.SNLST.Hhc.VLGKLSC(BAT)ELHKLQTYPRTNTGSGTP.amide | (SEQ ID NO: 4) 3679* | 3877* |
| 2. CH₃CO.SNLST.Hhc.VLGKLSQELHKLQTYPRTNTGSGTP(ε-K)GC.amide | (SEQ ID NO: 13) 3687* | 3886 |
| 3. CH₃CO.SNLST.Hhc.VLGKLSCELHKLQTYPRTNTGSGTP.amide | (SEQ ID NO: 5) 3373* | NA |

TABLE I-continued

| Peptide | | Peptide | ReO Complex |
|---|---|---|---|
| 4. CH$_3$CO.SNLST.Hhc.VLGKLSC(CH$_2$CO.GGCK.amide)ELHKLQTYPRTNTGSGTP.amide | (SEQ ID NO: 14) | 3873* | 4078 |
| 5. CH$_3$CO.SNLST.Hhc.VLGKLSC(CH$_2$CO.(β-Dap)KCK.amide)ELHKLQTYPRTNTGSGTP.amide | (SEQ ID NO: 15) | 3777* | 3975 |
| 6. CH$_3$CO.SNLST.Hhc.VLGKLSC(CH$_2$CO.(ε-K)GCE.amide)ELHKLQTYPRTNTGSGTP.amide | (SEQ ID NO: 16) | 3849* | 4047 |
| 7. CH$_3$CO.SNLST.Hcy.VLGKLSCELHKLQTYPRTNTGSGTP.amide | (SEQ ID NO: 6) | 3360* | NA |
| 8. CH$_3$CO.SNLST.Hcy.VLGKLSC(CH$_2$CO.GGCK.amide)ELHKLQTYPRTNTGSGTP.amide | (SEQ ID NO: 17) | 3762* | 3962 |
| 9. CH$_3$CO.SNLST.Hcy.VLGKLSC(CH$_2$CO.(β-Dap)KCK.amide)ELHKLQTYPRTNTGSGTP.amide | (SEQ ID NO: 18) | 3862* | 4063 |
| 10. CH$_3$CO.SNLST.Hcy.VLGKLSC(CH$_2$CO.(ε-K)GCE.amide)ELHKLQTYPRTNTGSGTP.amide | (SEQ ID NO: 19) | 3835* | 4033 |
| 11. CH$_3$CO.SNLST.Cys.VLGKLSCELHKLQTYPRTNTGSGTP.amide | (SEQ ID NO: 7) | 3346* | NA |
| 12. CH$_3$CO.SNLST.Cys.VLGKLSC(CH$_2$CO.GGCK.amide)ELHKLQTYPRTNTGSGTP.amide | (SEQ ID NO: 20) | 3748* | 3947 |
| 13. CH$_3$CO.SNLST.Cys.VLGKLSC(CH$_2$CO.(β-Dap)KCK.amide)ELHKLQTYPRTNTGSGTP.amide | (SEQ ID NO: 21) | 3848* | 4048 |
| 14. CH$_3$CO.SNLST.Cys.VLGKLSC(CH$_2$CO.(ε-K)GCE.amide)ELHKLQTYPRTNTGSGTP.amide | (SEQ ID NO: 22) | 3820 | 4019 |
| 15. SNLST.Asu.VLGKLSCELHKLQTYPRTNTGSGTP.amide | (SEQ ID NO: 8) | 3356 | NA |
| 16. SNLST.Asu.VLGKLSC(CH$_2$CO.(β-Dap)KCK.amide)ELHKLQTYPRTNTGSGTP.amide | (SEQ ID NO: 23) | 3858 | 4057 |
| 17. SNLST.Asu.VLGKLSCELHKLQTYPRTDVGAGTP.amide | (SEQ ID NO: 25) | 3338 | NA |
| 18. SNLST.Asu.VLGKLSC(CH$_2$CO.(β-Dap)KCK.amide)ELHKLQTYPRTDVGAGTP.amide | (SEQ ID NO: 24) | 3841 | 4040 |

*= M$^+$ determined by electrospray mass spectrometry
M$^+$ determined by fast atom bombardment mass spectrometry for all other peptides.

EXAMPLE 3

A General Method for Radiolabeling with Technetium-99m 0.1 mg of a peptide prepared as in Example 2 was dissolved in 0.1 mL or 0.2 mL of water or 0.9% saline. Technetium-99m gluceptate was prepared by reconstituting a Glucoscan vial (E.I. DuPont de Nemours, Inc., Wilmington, Del.) with 0.25 mL of Technetium-99m sodium pertechnetate containing up to 200 mCi and allowed to stand for 15 minutes at room temperature. 25 μl of Technetium-99m gluceptate was then added to the peptide and the reaction allowed to proceed at room temperature for 15 to 60 min or at 100° C. for 10 to 30 min, and then filtered through a 0.2 μm filter.

The Technetium-99m labeled peptide purity was determined by reverse-phase HPLC using the following conditions: a Waters Delta Pak C-18, 5μ, 3.9 mm×150 mm analytical column was loaded with each radiolabeled peptide, and the peptides eluted at a solvent flow rate equal to 1 mL/min (Delta-Pak). Gradient elution was performed using a gradient of 20–50% Solvent B/Solvent A (Solvent A is 0.1% CF$_3$CoOH in water and Solvent B is 0.1% CF$_3$CoOH in 90/10 CH$_3$CN/H$_2$O) for 20 min., followed by 100% B/A for 3 min.

Radioactive components were detected using an in-line radiometric detector linked to an integrating recorder. Technetium-99m gluceptate and Technetium-99m sodium pertechnetate elute between 1 and 4 minutes under these conditions, whereas the Technetium-99m labeled peptides eluted after a much greater amount of time. Peptides were detected by in4ine spectrophotometric detection at 220 nm.

Non-radioactive rhenium complexes were prepared by co-dissolving each of the peptide reagents of the invention with about one molar equivalent of tetrabutylammonium oxotetrabromorhenate (+5), prepared as described by cotton et al. (1966, *Inorg. Chem.* 5: 9–16) in dimethylformamide or acetonitrile/water and stirred for 0.5–5 days. The rhenium complexes were isolated by reverse phase HPLC as described above for Technetium-99m labeled peptides and were characterized by FABMS or ESMS. Non-radioactive peptides were detected as peptides by in-line spectrophotometric detection at 220 nm.

Radioactive rhenium complexes, using for example Re-186 or Re-188, are prepared from the appropriate perrhenate salts using the same protocol as for Technetium-99m labeling, or by adding a reducing agent to a solution of the peptide and perrhenate, or optionally using a ligand transfer agent such as citrate and incubating the reaction at a temperature between room temperature and 100° C. for between 5 and 60 min.

Results of HPLC purification of peptides, Technetium-99m labeled peptides and ReO-complexed peptides are shown in Table II.

TABLE II

| Peptide | | Peptide | ReO Complex |
|---|---|---|---|
| 1. CH$_3$CO.SNLST.Hhc.VLGKLSC(BAT)ELHKLQTYPRTNTGSGTP.amide | (SEQ ID NO: 4) | 13.7 | 15.6 |
| 2. CH$_3$CO.SNLST.Hhc.VLGKLSQELHKLQTYPRTNTGSGTP(ε-K)GC.amide | (SEQ ID NO: 13) | 15.0 | 13.5 |
| 3. CH$_3$CO.SNLST.Hhc.VLGKLSCELHKLQTYPRTNTGSGTP.amide | (SEQ ID NO: 5) | 19.2 | NA |
| 4. CH$_3$CO.SNLST.Hhc.VLGKLSC(CH$_2$CO.GGCK.amide)ELHKLQTYPRTNTGSGTP.amide | (SEQ ID NO: 14) | 21.2 | 17.8 |
| 5. CH$_3$CO.SNLST.Hhc.VLGKLSC(CH$_2$CO.(β-Dap)KCK.amide)ELHKLQTYPRTNTGSGTP.amide | (SEQ ID NO: 15) | 12.1 | 12.9 |
| 6. CH$_3$CO.SNLST.Hhc.VLGKLSC(CH$_2$CO.(ε-K)GCE.amide)ELHKLQTYPRTNTGSGTP.amide | (SEQ ID NO: 16) | 11.9 | 12.4 |
| 7. CH$_3$CO.SNLST.Hcy.VLGKLSCELHKLQTYPRTNTGSGTP.amide | (SEQ ID NO: 6) | 13.1 | NA |
| 8. CH$_3$CO.SNLST.Hcy.VLGKLSC(CH$_2$CO.GGCK.amide)ELHKLQTYPRTNTGSGTP.amide | (SEQ ID NO: 17) | 12.4 | 13.5 |
| 9. CH$_3$CO.SNLST.Hcy.VLGKLSC(CH$_2$CO.(β-Dap)KCK.amide)ELHKLQTYPRTNTGSGTP.amide | (SEQ ID NO: 18) | 11.0 | 11.8 |
| 10. CH$_3$CO.SNLST.Hcy.VLGKLSC(CH$_2$CO.(ε-K)GCE.amide)ELHKLQTYPRTNTGSGTP.amide | (SEQ ID NO: 19) | 12.5 | 13.1 |
| 11. CH$_3$CO.SNLST.Cys.VLGKLSCELHKLQTYPRTNTGSGTP.amide | (SEQ ID NO: 7) | 10.7 | NA |
| 12. CH$_3$CO.SNLST.Cys.VLGKLSC(CH$_2$CO.GGCK.amide)ELHKLQTYPRTNTGSGTP.amide | (SEQ ID NO: 20) | 9.98 | 11.1 |
| 13. CH$_3$CO.SNLST.Cys.VLGKLSC(CH$_2$CO.(β-Dap)KCK.amide)ELHKLQTYPRTNTGSGTP.amide | (SEQ ID NO: 21) | 8.23 | 9.2 |
| 14. CH$_3$CO.SNLST.Cys.VLGKLSC(CH$_2$CO.(ε-K)GCE.amide)ELHKLQTYPRTNTGSGTP.amide | (SEQ ID NO: 22) | 9.98 | 10.7 |
| 15. SNLST.Asu.VLGKLSCELHKLQTYPRTNTGSGTP.amide | (SEQ ID NO: 8) | 12.7 | NA |
| 16. SNLST.Asu.VLGKLSC(CH$_2$CO.(β-Dap)KCK.amide)ELHKLQTYPRTNTGSGTP.amide | (SEQ ID NO: 23) | 10.7 | 11.4 |

TABLE II-continued

| Peptide | | Peptide | ReO Complex |
|---|---|---|---|
| 17. SNLST.Asu.VLGKLSCELHKLQTYPRTDVGAGTP.amide | (SEQ ID NO: 25) | 13.2 | NA |
| 18. SNLST.Asu.VLGKLSC(CH$_2$CO.(β-Dap)KCK.amide)ELHKLQTYPRTDVGAGTP.amide | (SEQ ID NO: 24) | 11.1 | 11.7 |

Data represents HPLC retention times in minutes.

EXAMPLE 4

Biological Assays

A. Binding Inhibition Assays

Peptide reagents within the scope of the invention, or ReO complexed embodiments thereof, were tested using in vitro assays that measure their ability to inhibit the specific binding of $^{125}$I-CT to the CT receptor, using membranes from rat brain or from a breast tumor cell line, and on whole cells from breast tumor cell lines, as described in detail below.

Assays using microsomal membrane fractions of rat brain and T-47D cells (obtained from the American Type Culture collection, Rockville, Md., ATCC Accession No. HTB-133) were used to identify analogs with high affinity for the CT receptor according to the method of Fisher et al. (1977, *British J. Cancer* 35: 777–784). Briefly, tissue was minced and homogenized. The membranes were washed several times, assayed for protein content and used in the binding assay. Membrane protein was incubated with 0.1 μCi of $^{125}$I-salmon CT (Amersham, Cleveland, Ohio) in he presence or absence of varying concentrations of reagents to be tested. Both uncomplexed and ReO complexed reagents were tested. One hundred percent specific binding of $^{125}$I-CT to the CT receptor was defined as the difference between total $^{125}$I-CT binding and nonspecific binding of $^{125}$I-CT measured in the presence of a receptor-saturating concentration (1 μM) of excess unlabeled salmon CT (Sigma, St. Louis, Mo.). The concentration at which the tested reagents inhibited specific binding of $^{125}$I-CT by 50% was defined as the IC$_{50}$.

Results of binding to membrane preparations of CT receptors for each of the tested reagents are shown in Table III. These results indicate that peptide reagents within the scope of the invention and ReO complexes of such reagents bind with high affinity to CT receptor-expressing tumor cell and brain membranes.

Similar experiments were performed with additional peptide reagents within the scope of the invention, using whole T47D cells and MCF-7 cells (ATCC Accession No. HTB-22). The cell binding assays were done essentially by the method of Findlay et al. (1990, *J. Endocrino.* 130: 321–326). Briefly, cells were washed in saline and resuspended in Hank's balanced salt solution. One to two million cells were incubated with 0.1 μCi $^{125}$I-salmon CT in the absence and presence of 1 μM unlabeled salmon CT to determine a 100% specific binding value. Cells were incubated with 0.1 μCi of $^{125}$I-CT in the presence or absence of varying concentrations of reagents to be tested, in uncomplexed and/or ReO-complexed form. IC$_{50}$ values were determined as described above. Results for each of the tested reagents are shown in Table IV.

TABLE III

Displacement of $^{125}$I-CT from CTR in T-47D and Rat Brain Membranes by CT-Mimetic Peptides

| | Peptide Structure | T-47D IC$_{50}$ | T-47D K$_i$ | Rat brain IC$_{50}$ | Rat brain K$_i$ |
|---|---|---|---|---|---|
| (SEQ ID NO: 4) | 1. (CH$_2$CO.SNLST.Hhc).VLGKLSC(BAT)ELHKLQTYPRTNTGSGTP.amide | 0.53 | 0.41 | 2.6 | ND |
| (SEQ ID NO: 13) | 2. (CH$_2$CO.SNLST.Hhc).VLGKLSQELHKLQTYPRTNTGSGTP(ε-K)GC.amide | 16 | 12 | 18 | ND |
| (SEQ ID NO: 4) | 1. (CH$_2$CO.SNLST.Hhc).VLGKLSC(BAT)ELHKLQTYPRTNTGSGTP.amide(ReO) | 1.5 | 1.2 | 3.0 | ND |
| (SEQ ID NO: 13) | 2. (CH$_2$CO.SNLST.Hhc).VLGKLSQELHKLQTYPRTNTGSGTP(ε-K)GC.amide(ReO) | 28 | 22 | 22 | ND |

TABLE IV

Displacement of $^{125}$I-CT from T47D (Cells and Membranes) and MCF-7 Cells

| | Sequence | IC$_{50}$ (nM)$^x$ | IC$_{50}$ (nM)$^y$ | IC$_{50}$ (nM)$^z$ |
|---|---|---|---|---|
| (SEQ ID NO: 5) | 3. CH$_2$CO.SNLST.Hhc.VLGKLSCELHKLQTYPRTNTGSGTP.amide | 1.6 | nd | nd |
| (SEQ ID NO: 14) | 4. CH$_2$CO.SNLST.Hhc.VLGKLSC(CH$_2$CO.GGCK.amide)ELHKLQTYPRTNTGSGTP.amide | 2.6 | nd | nd |
| (SEQ ID NO: 15) | 5. CH$_2$CO.SNLST.Hhc.VLGKLSC(CH$_2$CO.(β-Dap)KCK.amide)ELHKLQTYPRTNTGSGTP.amide.ReO | nd | 0.42 | 5.8 |
| (SEQ ID NO: 16) | 6. CH$_2$CO.SNLST.Hhc.VLGKLSC(CH$_2$CO.(ε-K)GCE.amide)ELHKLQTYPRTNTGSGTP.amide.ReO | nd | 0.33 | 3.3 |
| (SEQ ID NO: 17) | 8. CH$_2$CO.SNLST.Hcy.VLGKLSC(CH$_2$CO.GGCK.amide)ELHKLQTYPRTNTGSGTP.amide.ReO | nd | 0.83 | 4.8 |
| (SEQ ID NO: 18) | 9. CH$_2$CO.SNLST.Hcy.VLGKLSC(CH$_2$CO.(β-Dap)KCK.amide)ELHKLQTYPRTNTGSGTP.amide.ReO | nd | 0.84 | nd |
| (SEQ ID NO: 19) | 10. CH$_2$CO.SNLST.Hcy.VLGKLSC(CH$_2$CO.(ε-K)GCE.amide)ELHKLQTYPRTNTGSGTP.amide.ReO | nd | 0.89 | nd |
| (SEQ ID NO: 20) | 12. CH$_2$CO.SNLST.Cys.VLGKLSC(CH$_2$CO.GGCK.amide)ELHKLQTYPRTNTGSGTP.amide.ReO | nd | 1.0 | 5.2 |
| (SEQ ID NO: 21) | 13. CH$_2$CO.SNLST.Cys.VLGKLSC(CH$_2$CO.(β-Dap)KCK.amide)ELHKLQTYPRTNTGSGTP.amide.ReO | nd | 2.9 | nd |
| (SEQ ID NO: 22) | 14. CH$_2$CO.SNLST.Cys.VLGKLSC(CH$_2$CO.(ε-K)GCE.amide)ELHKLQTYPRTNTGSGTP.amide.ReO | nd | 2.6 | 1.9 |

TABLE IV-continued

Displacement of $^{125}$I-CT from T47D (Cells and Membranes) and MCF-7 Cells

| Sequence | IC$_{50}$ (nM)$^x$ | IC$_{50}$ (nM)$^y$ | IC$_{50}$ (nM)$^z$ |
|---|---|---|---|
| (SEQ ID NO: 23) 16. SNLST.Asu.VLGKLSC(CH$_2$CO.(β-Dap)KCK.amide)ELHKLQTYPRTNTGSGTP.amide.ReO | nd | 2.7 | 8.0 |
| (SEQ ID NO: 25) 18. SNLST.Asu.VLGKLSC(CH$_2$CO.(β-Dap)KCK.amide)ELHKLQTYPRTDVGAGTP.amide.ReO | nd | 0.55 | 7.0 |
| CSNLSTCVLGKLSQELHKLQTYPRTNTGSGTP-NH$_2$ (salmon calcitonin) (SEQ ID NO: 2) | nd | nd | 12.3 | nd = not done
wherein:
$^x$T-47D cell membranes
$^y$Whole T-47D cells..
$^z$Whole MCF-7 cells These results indicated that peptide reagents within the scope of the invention and ReO complexes of such peptides were capable of specifically binding to CT receptors on whole cells and that the reagents were potent inhibitors of CT binding in two different CT receptor-expressing breast tumor cell lines.

B. CT Receptor Expression in Breast Cancer Cell Lines

The binding of $^{125}$I-CT to whole cells was used to assess the CT receptor density in seven different human breast cancer cell lines. The site density per cell was determined for MCF-7 cells in the presence of different concentrations of CT to achieve saturation of the receptors. The data was then linearized by the method of Scatchard et al. (1949, N.Y. Acad. Sci. 51: 600–672) to estimate receptor density. Briefly, the saturation curves were linearized and the K$_d$ was calculated as (–1/slope), and the B$_{max}$ was equal to the x-axis intercept of the curve. Other cell lines (each of which was obtained from the ATCC, Rockville, Md.) were compared to MCF-7 cells at a single concentration of $^{125}$I-CT and their CT receptor density estimated thereby. The data are summarized in Table V.

TABLE V

| Cell Line | CT Receptors/Cell × 10$^{-3}$ |
|---|---|
| Du4475 | 21.5 |
| ZR75 | 39.5 |
| MDA-MB-157 | 51.0 |
| MCF-7 | 1,000 |
| Bt474 | 166 |
| HS578T | 0 |
| T-47D | 360 |

These data show that 86% (6 of 7) of the breast cancer cell lines assayed were positive for CT receptors. Thus, the target receptor for the reagents of the invention is present in most breast cancer cell lines tested. Recently, the target receptor for the reagents of the invention was found to be overexpressed in primary breast cancers (Gillespie, et al. (1997) *Int. J. Cancer* 73, 812–815). These results indicate that the CT peptides of the invention are appropriate for preparing useful site specific reagents for diagnosis and treatment of tumors in humans.

C. In vivo Assay

Breast cancer cell lines were screened for receptor expression and the best cell lines chosen for xenograft implantation in immune deficient mice. These tumor models were used to evaluate the tumor targeting potential in vivo of the high affinity peptides identified in the in vitro assays above.

CT receptor expressing breast cancer cells (T47D and MCF-7) were implanted into immune deficient mice or Sprague-Dawley rats and allowed to grow tumors. For testing new $^{99m}$Tc-CT peptides, tumor-bearing mice or rats were injected with approximately 0.025 mCi at approximately 6 mCi/10 nmol peptide. The animals were cervically dislocated and imaged statically for 5 minutes using a gamma camera. The biodistribution of the $^{99m}$Tc-CT peptide was then determined by counting blood, tumor, target organs and muscle in a gamma counter along with standard aliquots of the injected dose. The time points for biodistribution were chosen to represent early, middle and late phases of $^{99m}$Tc-CT analog clearance. Biodistribution studies indicated that optimal signal to noise ratios occurred at 90 minutes post-injection. To assess the tumor imaging potential of selected analogs, the ratio of radioactivity in blood and various tissues were compared to that in tumor. Representative biodistribution data after 90 minutes are shown in Table VI below.

TABLE VI

| | | Tumor | | | Biodistribution | | | | | PK (min) | |
|---|---|---|---|---|---|---|---|---|---|---|---|
| | | | | | Blood | Lung | GI tract | Liver | Kidneys | | |
| Peptide | Species | (% ID/g) | Tum:Bld | Tum:Con | (% ID/g) | (% ID) | (% ID) | (% ID) | (% ID) | t½$_\alpha$ | t½$_\beta$ |
| 8 | mouse$^b$ | 0.42 | 2.8 | 2.8 | 0.16 | 1.23% ID/g | | | | | |
| 8 | rat | | | | 0.026 | 0.10% ID/g | 4.8 | 3.7 | 45.6 | 1.6? | 20? |
| 2 | mouse$^a$ | 1.6 | 3.3 | 10 | | 0.24 | 5.4 | 5.5 | 18 | | |
| 4 | rat | | | | 0.027 | 0.53 | 2.0 | 4.0 | 35 | 1.4 | 19 |
| 5 | rat | | | | 0.048 | 0.56 | 4.5 | 5.8 | 31 | 1.6 | 17 |
| 6 | rat | | | | 0.044 | 0.10 | 1.8 | 2.5 | 32.2 | 1.6 | 21 |
| 6 | rabbit | | | | 0.012 | 0.20 | 5.3 | 2.3 | 14.1 | | |
| 6$^c$ | mouse$^b$ | 2.0 | 9.9 | 25 | 0.23 | 2.5% ID/g | | | | 3.1 | 25.9 |
| 6$^c$ | mouse$^b$ | 3.9 | 4.2 | 2.5 | 0.94 | 6.5% ID/g | | 2.7 | 53 | | |

TABLE VI-continued

| | | Tumor | | | Biodistribution | | | | | PK (min) | |
|---|---|---|---|---|---|---|---|---|---|---|---|
| | | | | | Blood | Lung | GI tract | Liver | Kidneys | | |
| Peptide | Species | (% ID/g) | Tum:Bld | Tum:Con | (% ID/g) | (% ID) | (% ID) | (% ID) | (% ID) | $t\frac{1}{2}_\alpha$ | $t\frac{1}{2}_\beta$ |
| 6 | mouse[a] | 1.5 | 1.6 | 2.1 | 0.91 | 2.3% ID/g | | 1.5 | 27 | | |

Peptide numbering corresponds to that of Tables I through IV.
[a]T-47D tumor in nude mouse
[b]MCF-7 breast cancer xenograft in nude mouse
[c]Different preparations It should be understood that the foregoing disclosure emphasizes certain specific embodiments of the invention and that all modifications or alternatives equivalent thereto are within the spirit and scope of the invention as set forth in the appended claims.

---

We claim:
1. A synthetic, calcitonin receptor-binding compound having a molecular weight of less than about 10,000 daltons and being covalently linked to a radiometal chelator to form a reagent wherein:
said reagent has a binding affinity for a calcitonin receptor equal to or greater than the binding affinity of radioiodinated native calcitonin for said receptor; and
the chelator is selected from the group consisting of:
(a) diethylenetriaminepentaacetic acid (DTPA);
(b) $(HOOCCH_2)_3N(CR_2)(CR_2)N(CH_2CoOH)(CR_2)(CR_2)N(CH_2CoOH)$;
where each R is independently H, $C_1$ to $C_4$ alkyl, or aryl and one R is covalently linked to a bivalent linker;
(c) ethylenediaminetetraacetic acid (EDTA);
(d) $(HOOCCH_2)_2N(CR_2)(CR_2)N(CH_2CoOH)$;
where each R is independently H, $C_1$ to $C_4$ alkyl, or aryl and one R is covalently linked to a bivalent linker;
(e) 1,4,7,10-tetraazadodecanetetraacetic acid;
(f)

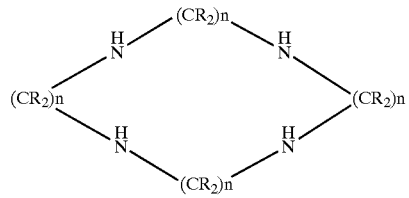

where n is an integer that is 2 or 3 and where each R is independently H, $C_1$ to $C_4$ alkyl, or aryl and one R is covalently linked to the calcitonin receptor binding compound, and
(g) desferrioxamine.
2. The reagent of claim 1, wherein the compound is a peptide.
3. The reagent of claim 2, wherein the peptide has an amino acid sequence (SEQ ID NO: 5)

CH$_2$Co.SNLST.Hhc. VLGKLSCELHKLQTYPRTNTGSGTP.amide and the chelator is incorporated into the peptide at a sidechain of an amino acid of said sequence.
4. The reagent of claim 2, wherein the peptide comprises a calcitonin receptor-binding domain which is cyclized by a thioether.
5. The reagent of claim 4, wherein the peptide comprises an amino acid sequence: (SEQ ID NO: 10)

CH$_2$Co.SNLSTX— wherein X is selected from the group consisting of a cysteine, a homocysteine, and a homohomocysteine.
6. A reagent of claim 4, wherein the peptide comprises an amino acid sequence: (SEQ ID NO: 11)

CH$_2$Co.X1NLSTX$_2$— wherein $X^1$ is selected from the group consisting of an alanine, a glycine, and a serine; and
$X^2$ is selected from the group consisting of a cysteine, a homocysteine, and a homohomocysteine.
7. A radiotherapeutic agent comprising the reagent of any of claims 1 through 6 and a cytotoxic radioisotope.

8. The agent of claim 7, wherein the radioisotope is selected from the group consisting of scandium-47, copper-67, gallium-72, yttrium-90, tin-117m, iodine-125, iodine-131, samarium-153, gadolinium-159, dysprosium-165, holmium-166, ytterbium-175, lutetium-177, rhenium-186, rhenium-188, astatine-211, bismuth-212, and bismuth-213.
9. A kit for preparing a radiopharmaceutical preparation, said kit comprising a sealed vial containing a predetermined quantity of the reagent of any of claims 1 through 6.
10. A method of treating a mammal for a disease characterized by the presence of calcitonin receptors comprising the step of administering a therapeutically effective amount of the agent of claim 8 to said mammal.
11. A synthetic, calcitonin receptor-binding compound having a molecular weight of less than about 10,000 daltons and being covalently linked to a radiometal chelator to form a reagent characterized in that:
said reagent has a binding affinity for a calcitonin receptor of not less than about one-tenth the binding affinity of radioiodinated native calcitonin for said receptor wherein the chelator is selected from the group consisting of:
(a) diethylenetriaminepentaacetic acid (DTPA);
(b) $(HOOCCH_2)_2N(CR_2)(CR_2)N(CH_2CoOH)(CR_2)(CR_2)N(CH_2CoOH)$
where each R is independently H, $C_1$ to $C_4$ alkyl, or aryl and one R is covalently linked to a bivalent linker;
(c) ethylenediaminetetraacetic acid (EDTA);
(d) $(HOOCCH_2)_2N(CR_2)(CR_2)N(CH_2CoOH)$;
where each R is independently H, $C_1$ to $C_4$ alkyl, or aryl and one R is covalently linked to a bivalent linker;
(e) 1,4,7,10-tetraazadodecanetetraacetic acid;

(f)

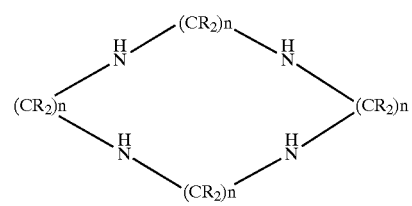

where n is an integer that is 2 or 3 and where each R is independently H, $C_1$ to $C_4$ alkyl, or aryl and one R is covalently linked to the calcitonin receptor binding compound, and
(g) desferrioxamine.
12. The reagent of claim 11, wherein the compound is a peptide.
13. The reagent of claim 11, wherein the peptide has an amino acid sequence CH$_2$Co.SNLST.Hhc.VLGKLSCELHKLQTYPRTNTGSGTP.amide and the chelator is incorporated into the peptide at a sidechain of an amino acid of said sequence.
14. The reagent of claim 12, wherein the peptide comprises a calcitonin receptor-binding domain which is cyclized by a thioether.
15. The reagent of claim 14, wherein the peptide comprises an amino acid sequence:

CH$_2$Co.SNLSTX— wherein X is selected from the group consisting of a cysteine, a homocysteine, and a homohomocysteine.

16. The reagent of claim 14, wherein the peptide comprises an amino acid sequence:

$CH_2Co.X^1NLSTX^2-$ wherein $X^1$ is selected from the group consisting of an alanine, a glycine, and a serine; and $X^2$ is selected from the group consisting of a cysteine, a homocysteine, and a homohomocysteine.

17. A radiotherapeutic agent comprising the reagent of any of claims 11 through 16 and a cytotoxic radioisotope.

18. The reagent of claim 17, wherein the peptide has an amino acid sequence (SEQ ID NO: 5)

$CH_2Co.SNLST.Hhc. VLGKLSCELHKLQTYPRTNTGSGTP.amide$ and the chelator is incorporated into the peptide at a sidechain of an amino acid of said sequence.

19. A kit for preparing a radiopharmaceutical preparation, said kit comprising a sealed vial containing a predetermined quantity of the reagent of any of claims 11 through 16.

20. The reagent of claim 19, wherein the peptide comprises an amino acid sequence: (SEQ ID NO: 10)

$CH_2Co.SNLSTX-$ wherein X is selected from the group consisting of a cysteine, a homocysteine, and a homohomocysteine.

* * * * *

UNITED STATES PATENT AND TRADEMARK OFFICE
CERTIFICATE OF CORRECTION

PATENT NO. : 6,509,001 B1
APPLICATION NO. : 09/553494
DATED : January 21, 2003
INVENTOR(S) : Dean et al.

It is certified that error appears in the above-identified patent and that said Letters Patent is hereby corrected as shown below:

Column 41, line 11, reads "($CH_2CoOH$)" should read -- ($CH_2COOH$) --
Column 41, line 12, reads "($CH_2CoOH$)" should read -- ($CH_2COOH$) --
Column 41, line 17, reads "($CH_2CoOH$)" should read -- ($CH_2COOH$) --
Column 41, line 43, reads "$CH_2Co.SNLST$." should read -- $CH_2CO.SNLST$. --
Column 41, line 53, reads "$CH_2Co.SNLSTX-$" should read -- $CH_2CO.SNLSTX-$ --
Column 41, line 60, reads "$CH_2Co.X1NLSTX_2-$" should read -- $CH_2CO.X^1NLSTX^2-$ --
Column 42, line 24, reads "($CH_2CoOH$)" should read -- ($CH_2COOH$) --
Column 42, line 25, reads "($CH_2CoOH$)" should read -- ($CH_2COOH$) --
Column 42, line 30, reads "($CH_2CoOH$)" should read -- ($CH_2COOH$) --
Column 42, line 56, reads "$CH_2Co.SNLST$." should read -- $CH_2CO.SNLST$. --
Column 42, line 65, reads "$CH_2Co.SNLSTX-$" should read -- $CH_2CO.SNLSTX-$ --
Column 43, line 4, reads "$CH_2Co.X1NLSTX_2-$" should read -- $CH_2CO.X^1NLSTX^2-$ --
Column 43, line 15, reads "$CH_2Co.SNLST$." should read -- $CH_2CO.SNLST$. --
Column 44, line 10, reads "$CH_2Co.SNLSTX-$" should read -- $CH_2CO.SNLSTX-$ --

Signed and Sealed this

Thirty-first Day of July, 2007

JON W. DUDAS
*Director of the United States Patent and Trademark Office*

SEQUENCE LISTING

<160> NUMBER OF SEQ ID NOS: 26

<210> SEQ ID NO 1
<211> LENGTH: 32
<212> TYPE: PRT
<213> ORGANISM: Homo sapiens
<220> FEATURE:
<223> OTHER INFORMATION: C-term amidated

<400> SEQUENCE: 1

Cys Gly Asn Leu Ser Thr Cys Met Leu Gly Thr Tyr Thr Gln Asp Phe
 1               5                  10                  15

Asn Lys Phe His Thr Phe Pro Gln Thr Ala Ile Gly Val Gly Ala Pro
             20                  25                  30

<210> SEQ ID NO 2
<211> LENGTH: 32
<212> TYPE: PRT
<213> ORGANISM: Salmonis sp.
<220> FEATURE:
<223> OTHER INFORMATION: C-term amidated

<400> SEQUENCE: 2

Cys Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Ser Gly Thr Pro
             20                  25                  30

<210> SEQ ID NO 3
<211> LENGTH: 32
<212> TYPE: PRT
<213> ORGANISM: Anguilla sp.
<220> FEATURE:
<223> OTHER INFORMATION: C-term amidated

<400> SEQUENCE: 3

Cys Ser Asn Leu Ser Thr Cys Val Leu Gly Lys Leu Ser Gln Glu Leu
 1               5                  10                  15

His Lys Leu Gln Thr Tyr Pro Arg Thr Asp Val Gly Ala Gly Thr Pro
             20                  25                  30

<210> SEQ ID NO 4
<211> LENGTH: 31
<212> TYPE: PRT
<213> ORGANISM: Artificial Sequence

```
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homohomocysteine
<223> OTHER INFORMATION: The thiol group of cysteine 13 is attached to a
      bisamino bisthiol chelator
<223> OTHER INFORMATION: C-term amidated

<400> SEQUENCE: 4

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homohomocysteine
<223> OTHER INFORMATION: C-term amidated

<400> SEQUENCE: 5

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homocysteine
<223> OTHER INFORMATION: C-term amidated

<400> SEQUENCE: 6

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: C-term amidated

<400> SEQUENCE: 7

Ser Asn Leu Ser Thr Cys Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30
```

```
<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: 2-amino suberic acid between positions 5 and 6
<223> OTHER INFORMATION: C-term amidated

<400> SEQUENCE: 8

Ser Asn Leu Ser Thr Val Leu Gly Lys Leu Ser Cys Glu Leu His Lys
 1               5                  10                  15

Leu Gln Thr Tyr Pro Arg Thr Asn Thr Gly Ser Gly Thr Pro
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homohomocysteine
<223> OTHER INFORMATION: C-term amidated

<400> SEQUENCE: 9

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Cysteine, homocysteine or homohomocysteine

<400> SEQUENCE: 10

Ser Asn Leu Ser Thr Xaa
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ala, Gly or Ser
<221> NAME/KEY: MOD_RES
<222> LOCATION: (6)
<223> OTHER INFORMATION: Cysteine, homocysteine or homohomocysteine

<400> SEQUENCE: 11

Xaa Asn Leu Ser Thr Xaa
 1               5

<210> SEQ ID NO 12
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu His Lys Leu Gln Tyr
 1               5

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homohomocysteine
<221> NAME/KEY: MOD_RES
<222> LOCATION: (32)
<223> OTHER INFORMATION: Epsilon-Lys
<223> OTHER INFORMATION: C-term amidated

<400> SEQUENCE: 13

Ser Asn Leu Ser Thr Xaa Val Leu Gly Lys Leu Ser Gln Glu Leu His
 1               5                  10                  15

Lys Leu Gln Thr Tyr Pro Arg Thr Asn Thr Gly Ser Gly Thr Pro Xaa
            20                  25                  30

Gly Cys

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homohomocysteine
<223> OTHER INFORMATION: (CH2CO, GGCK.amide) between positions 13 and 14
<223> OTHER INFORMATION: C-term amidated

<400> SEQUENCE: 14

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homohomocysteine
<223> OTHER INFORMATION: (CH2CO.(Beta-Dap)KCK.amide) between positions
      13 and 14
<223> OTHER INFORMATION: C-term amidated

<400> SEQUENCE: 15

Ser Asn Leu Ser Thr Xaa Val Leu Gly Lys Leu Ser Cys Glu Leu His
 1               5                  10                  15
```

Lys Leu Gln Thr Tyr Pro Arg Thr Asn Thr Gly Ser Gly Thr Pro
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homohomocysteine
<223> OTHER INFORMATION: (CH2CO.(Epsilon-K)GCE.amide) between position
      13 and 14
<223> OTHER INFORMATION: C-term amidated

<400> SEQUENCE: 16

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homocysteine
<223> OTHER INFORMATION: (CH2CO.GGCK.amide) between positions 13 and 14
<223> OTHER INFORMATION: C-term amidated

<400> SEQUENCE: 17

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Homocysteine
<223> OTHER INFORMATION: (CH2CO.(Beta-Dap)KCK.amide) between positions
      13 and 14
<223> OTHER INFORMATION: C-term amidated

<400> SEQUENCE: 18

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

```
<221> NAME/KEY: MOD_RES
<222> LOCATION: (6)
<223> OTHER INFORMATION: Homocysteine
<223> OTHER INFORMATION: (CH2CO.(Epsilon-K)GCE.amide) between positions
      13 and 14
<223> OTHER INFORMATION: C-term amidated

<400> SEQUENCE: 19

Ser Asn Leu Ser Thr Xaa Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: (CH2CO.GGCK.amide) between positions 13 and 14
<223> OTHER INFORMATION: C-term amidated

<400> SEQUENCE: 20

Ser Asn Leu Ser Thr Cys Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: (CH2CO.(Beta-Dap)KCK.amide) between positions
      13 and 14
<223> OTHER INFORMATION: C-term amidated

<400> SEQUENCE: 21

Ser Asn Leu Ser Thr Cys Val Leu Gly Lys Leu Ser Cys Glu Leu His
 1               5                  10                  15

Lys Leu Gln Thr Tyr Pro Arg Thr Asn Thr Gly Ser Gly Thr Pro
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: (CH2CO.(Epsilon-K)GCE. amide) between positions
      13 and 14
<223> OTHER INFORMATION: C-term amidated

<400> SEQUENCE: 22

Ser Asn Leu Ser Thr Cys Val Leu Gly Lys Leu Ser Cys Glu Leu His
 1               5                  10                  15
```

```
Lys Leu Gln Thr Tyr Pro Arg Thr Asn Thr Gly Ser Gly Thr Pro
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: 2-amino suberic acid between positions 5 and 6
<223> OTHER INFORMATION: (CH2CO.(Beta-Dap)KCK.amide) between positions
      12 and 13
<223> OTHER INFORMATION: C-term amidated

<400> SEQUENCE: 23

Ser Asn Leu Ser Thr Val Leu Gly Lys Leu Ser Cys Glu Leu His Lys
  1               5                  10                  15

Leu Gln Thr Tyr Pro Arg Thr Asn Thr Gly Ser Gly Thr Pro
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: 2-amino suberic acid between positions 5 and 6
<223> OTHER INFORMATION: (CH2CO.(Beta-Dap)KCK.amide) between positions
      12 and 13
<223> OTHER INFORMATION: C-term amidated

<400> SEQUENCE: 24

Ser Asn Leu Ser Thr Val Leu Gly Lys Leu Ser Cys Glu Leu His Lys
  1               5                  10                  15

Leu Gln Thr Tyr Pro Arg Thr Asp Val Gly Ala Gly Thr Pro
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: 2-amino suberic acid between positions 5 and 6
<223> OTHER INFORMATION: C-term amidated

<400> SEQUENCE: 25

Ser Asn Leu Ser Thr Val Leu Gly Lys Leu Ser Cys Glu Leu His Lys
  1               5                  10                  15

Leu Gln Thr Tyr Pro Arg Thr Asp Val Gly Ala Gly Thr Pro
            20                  25                  30

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Cys Lys
  1
```